US012458745B2

(12) United States Patent
Long et al.

(10) Patent No.: US 12,458,745 B2
(45) Date of Patent: Nov. 4, 2025

(54) PIEZOELECTRIC PUMP ADAPTER FOR NEGATIVE-PRESSURE THERAPY

(71) Applicant: Solventum Intellectual Properties Company, Maplewood, MN (US)

(72) Inventors: Justin Alexander Long, Lago Vista, TX (US); Christopher Brian Locke, Bournemouth (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 448 days.

(21) Appl. No.: 17/297,960

(22) PCT Filed: Nov. 15, 2019

(86) PCT No.: PCT/US2019/061646
§ 371 (c)(1),
(2) Date: May 27, 2021

(87) PCT Pub. No.: WO2020/139475
PCT Pub. Date: Jul. 2, 2020

(65) Prior Publication Data

US 2022/0088288 A1 Mar. 24, 2022

Related U.S. Application Data

(60) Provisional application No. 62/784,901, filed on Dec. 26, 2018.

(51) Int. Cl.
*A61M 1/00* (2006.01)
*F04B 53/16* (2006.01)

(52) U.S. Cl.
CPC ............ *A61M 1/962* (2021.05); *F04B 53/16* (2013.01); *A61M 2205/3606* (2013.01)

(58) Field of Classification Search
CPC ...... F04B 45/047; F04B 43/04; F04B 43/046; F04B 53/16
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

English Machine Translation of JP-2011131042-A (Year: 2011).*
(Continued)

*Primary Examiner* — Nathan C Zollinger

(57) ABSTRACT

A system for negative-pressure therapy is described. The system includes a dressing configured to be positioned adjacent a tissue site and a piezoelectric pump having at least one inlet and at least one outlet. An adapter is coupled to the piezoelectric pump and configured to be fluidly coupled to the dressing. The adapter is configured to aggregate fluid flow into the at least one inlet. The adapter can have a block. A first recess depends into the block, and a second recess depends into the block from the first recess, the second recess having an area less than the area of the first recess. A bore depends through the block from the second recess to the first side, and a conduit is coupled to the first side and fluidly coupled to the bore.

18 Claims, 15 Drawing Sheets

(56) References Cited

U.S. PATENT DOCUMENTS

| | | | | |
|---|---|---|---|---|
| 2,632,443 | A | | 3/1953 | Lesher |
| 2,682,873 | A | | 7/1954 | Evans et al. |
| 2,910,763 | A | | 11/1959 | Lauterbach |
| 2,969,057 | A | | 1/1961 | Simmons |
| 3,066,672 | A | | 12/1962 | Crosby, Jr. et al. |
| 3,367,332 | A | | 2/1968 | Groves |
| 3,520,300 | A | | 7/1970 | Flower, Jr. |
| 3,568,675 | A | | 3/1971 | Harvey |
| 3,648,692 | A | | 3/1972 | Wheeler |
| 3,682,180 | A | | 8/1972 | McFarlane |
| 3,826,254 | A | | 7/1974 | Mellor |
| 4,080,970 | A | | 3/1978 | Miller |
| 4,096,853 | A | | 6/1978 | Weigand |
| 4,139,004 | A | | 2/1979 | Gonzalez, Jr. |
| 4,165,748 | A | | 8/1979 | Johnson |
| 4,184,510 | A | | 1/1980 | Murry et al. |
| 4,233,969 | A | | 11/1980 | Lock et al. |
| 4,245,630 | A | | 1/1981 | Lloyd et al. |
| 4,256,109 | A | | 3/1981 | Nichols |
| 4,261,363 | A | | 4/1981 | Russo |
| 4,275,721 | A | | 6/1981 | Olson |
| 4,284,079 | A | | 8/1981 | Adair |
| 4,297,995 | A | | 11/1981 | Golub |
| 4,333,468 | A | | 6/1982 | Geist |
| 4,373,519 | A | | 2/1983 | Errede et al. |
| 4,382,441 | A | | 5/1983 | Svedman |
| 4,392,853 | A | | 7/1983 | Muto |
| 4,392,858 | A | | 7/1983 | George et al. |
| 4,419,097 | A | | 12/1983 | Rowland |
| 4,465,485 | A | | 8/1984 | Kashmer et al. |
| 4,475,909 | A | | 10/1984 | Eisenberg |
| 4,480,638 | A | | 11/1984 | Schmid |
| 4,525,166 | A | | 6/1985 | Leclerc |
| 4,525,374 | A | | 6/1985 | Vaillancourt |
| 4,540,412 | A | | 9/1985 | Van Overloop |
| 4,543,100 | A | | 9/1985 | Brodsky |
| 4,548,202 | A | | 10/1985 | Duncan |
| 4,551,139 | A | | 11/1985 | Plaas et al. |
| 4,569,348 | A | | 2/1986 | Hasslinger |
| 4,605,399 | A | | 8/1986 | Weston et al. |
| 4,608,041 | A | | 8/1986 | Nielsen |
| 4,640,688 | A | | 2/1987 | Hauser |
| 4,655,754 | A | | 4/1987 | Richmond et al. |
| 4,664,662 | A | | 5/1987 | Webster |
| 4,710,165 | A | | 12/1987 | McNeil et al. |
| 4,733,659 | A | | 3/1988 | Edenbaum et al. |
| 4,743,232 | A | | 5/1988 | Kruger |
| 4,758,220 | A | | 7/1988 | Sundblom et al. |
| 4,787,888 | A | | 11/1988 | Fox |
| 4,826,494 | A | | 5/1989 | Richmond et al. |
| 4,838,883 | A | | 6/1989 | Matsuura |
| 4,840,187 | A | | 6/1989 | Brazier |
| 4,863,449 | A | | 9/1989 | Therriault et al. |
| 4,872,450 | A | | 10/1989 | Austad |
| 4,878,901 | A | | 11/1989 | Sachse |
| 4,897,081 | A | | 1/1990 | Poirier et al. |
| 4,906,233 | A | | 3/1990 | Moriuchi et al. |
| 4,906,240 | A | | 3/1990 | Reed et al. |
| 4,919,654 | A | | 4/1990 | Kalt |
| 4,941,882 | A | | 7/1990 | Ward et al. |
| 4,953,565 | A | | 9/1990 | Tachibana et al. |
| 4,969,880 | A | | 11/1990 | Zamierowski |
| 4,985,019 | A | | 1/1991 | Michelson |
| 5,037,397 | A | | 8/1991 | Kalt et al. |
| 5,086,170 | A | | 2/1992 | Luheshi et al. |
| 5,092,858 | A | | 3/1992 | Benson et al. |
| 5,100,396 | A | | 3/1992 | Zamierowski |
| 5,134,994 | A | | 8/1992 | Say |
| 5,149,331 | A | | 9/1992 | Ferdman et al. |
| 5,167,613 | A | | 12/1992 | Karami et al. |
| 5,176,663 | A | | 1/1993 | Svedman et al. |
| 5,215,522 | A | | 6/1993 | Page et al. |
| 5,232,453 | A | | 8/1993 | Plass et al. |
| 5,261,893 | A | | 11/1993 | Zamierowski |
| 5,278,100 | A | | 1/1994 | Doan et al. |
| 5,279,550 | A | | 1/1994 | Habib et al. |
| 5,298,015 | A | | 3/1994 | Komatsuzaki et al. |
| 5,342,376 | A | | 8/1994 | Ruff |
| 5,344,415 | A | | 9/1994 | DeBusk et al. |
| 5,358,494 | A | | 10/1994 | Svedman |
| 5,437,622 | A | | 8/1995 | Carion |
| 5,437,651 | A | * | 8/1995 | Todd ..................... A61M 1/915 604/323 |
| 5,527,293 | A | | 6/1996 | Zamierowski |
| 5,549,584 | A | | 8/1996 | Gross |
| 5,556,375 | A | | 9/1996 | Ewall |
| 5,607,388 | A | | 3/1997 | Ewall |
| 5,636,643 | A | | 6/1997 | Argenta et al. |
| 5,645,081 | A | | 7/1997 | Argenta et al. |
| 6,071,267 | A | | 6/2000 | Zamierowski |
| 6,135,116 | A | | 10/2000 | Vogel et al. |
| 6,241,747 | B1 | | 6/2001 | Ruff |
| 6,287,316 | B1 | | 9/2001 | Agarwal et al. |
| 6,345,623 | B1 | | 2/2002 | Heaton et al. |
| 6,488,643 | B1 | | 12/2002 | Tumey et al. |
| 6,493,568 | B1 | | 12/2002 | Bell et al. |
| 6,553,998 | B2 | | 4/2003 | Heaton et al. |
| 6,814,079 | B2 | | 11/2004 | Heaton et al. |
| 7,846,141 | B2 | | 12/2010 | Weston |
| 8,062,273 | B2 | | 11/2011 | Weston |
| 8,216,198 | B2 | | 7/2012 | Heagle et al. |
| 8,251,979 | B2 | | 8/2012 | Malhi |
| 8,257,327 | B2 | | 9/2012 | Blott et al. |
| 8,398,614 | B2 | | 3/2013 | Blott et al. |
| 8,449,509 | B2 | | 5/2013 | Weston |
| 8,529,548 | B2 | | 9/2013 | Blott et al. |
| 8,535,296 | B2 | | 9/2013 | Blott et al. |
| 8,551,060 | B2 | | 10/2013 | Schuessler et al. |
| 8,568,386 | B2 | | 10/2013 | Malhi |
| 8,679,081 | B2 | | 3/2014 | Heagle et al. |
| 8,834,451 | B2 | | 9/2014 | Blott et al. |
| 8,926,592 | B2 | | 1/2015 | Blott et al. |
| 9,017,302 | B2 | | 4/2015 | Vitaris et al. |
| 9,198,801 | B2 | | 12/2015 | Weston |
| 9,211,365 | B2 | | 12/2015 | Weston |
| 9,289,542 | B2 | | 3/2016 | Blott et al. |
| 9,427,505 | B2 | * | 8/2016 | Askem ................ F04B 43/0054 |
| 11,123,471 | B2 | * | 9/2021 | Askem .................. A61M 1/962 |
| 2002/0077661 | A1 | | 6/2002 | Saadat |
| 2002/0115951 | A1 | | 8/2002 | Norstrem et al. |
| 2002/0120185 | A1 | | 8/2002 | Johnson |
| 2002/0143286 | A1 | | 10/2002 | Tumey |
| 2009/0232683 | A1 | * | 9/2009 | Hirata ................... F04B 45/047 417/413.2 |
| 2011/0117465 | A1 | * | 5/2011 | Yajima .............. H01M 8/04007 429/434 |
| 2014/0163491 | A1 | | 6/2014 | Schuessler et al. |
| 2015/0080788 | A1 | | 3/2015 | Blott et al. |
| 2017/0112974 | A1 | | 4/2017 | Fujisaki |

FOREIGN PATENT DOCUMENTS

| | | | | | |
|---|---|---|---|---|---|
| AU | 755496 | B2 | | 12/2002 | |
| CA | 2005436 | A1 | | 6/1990 | |
| CN | 1372078 | A | * | 10/2002 | .......... F04B 11/0008 |
| DE | 26 40 413 | A1 | | 3/1978 | |
| DE | 43 06 478 | A1 | | 9/1994 | |
| DE | 29 504 378 | U1 | | 9/1995 | |
| EP | 0100148 | A1 | | 2/1984 | |
| EP | 0117632 | A2 | | 9/1984 | |
| EP | 0161865 | A2 | | 11/1985 | |
| EP | 0358302 | A2 | | 3/1990 | |
| EP | 1018967 | A1 | | 7/2000 | |
| GB | 692578 | A | | 6/1953 | |
| GB | 2195255 | A | | 4/1988 | |
| GB | 2 197 789 | A | | 6/1988 | |
| GB | 2 220 357 | A | | 1/1990 | |
| GB | 2 235 877 | A | | 3/1991 | |
| GB | 2 329 127 | A | | 3/1999 | |
| GB | 2 333 965 | A | | 8/1999 | |
| JP | 4129536 | B2 | | 8/2008 | |
| JP | 2011131042 | A | * | 7/2011 | ........ A61M 5/16804 |
| JP | 2016200067 | A | * | 12/2016 | |
| SG | 71559 | | | 4/2002 | |

(56) References Cited

FOREIGN PATENT DOCUMENTS

| | | | | | |
|---|---|---|---|---|---|
| WO | 80/02182 | A1 | | 10/1980 | |
| WO | 87/04626 | A1 | | 8/1987 | |
| WO | 90/010424 | A1 | | 9/1990 | |
| WO | 93/009727 | A1 | | 5/1993 | |
| WO | 94/20041 | A1 | | 9/1994 | |
| WO | 96/05873 | A1 | | 2/1996 | |
| WO | 97/18007 | A1 | | 5/1997 | |
| WO | 99/13793 | A1 | | 3/1999 | |
| WO | WO-2009050990 | A1 | * | 4/2009 | F04B 39/1093 |
| WO | WO-2009145064 | A1 | * | 12/2009 | F04B 43/043 |
| WO | WO-2009148008 | A1 | * | 12/2009 | F04B 43/046 |
| WO | WO-2011040320 | A1 | * | 4/2011 | F04B 43/046 |
| WO | 2012/057881 | A1 | | 5/2012 | |
| WO | 2016/008154 | A1 | | 1/2016 | |
| WO | 2018/056060 | A1 | | 3/2018 | |

OTHER PUBLICATIONS

English Machine Translation of JP-2016200067-A (Year: 2016).*
English Machine Translation of CN-1372078-A (Year: 2002).*
International Search Report and Written Opinion for Corresponding Application No. PCT/US2019/061646, mailed Jul. 9, 2020.
Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al.; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Bjöm et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

(56) References Cited

OTHER PUBLICATIONS

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

* cited by examiner

PIEZOELECTRIC PUMP ADAPTER FOR NEGATIVE-PRESSURE THERAPY

RELATED APPLICATIONS

The present application claims priority to U.S. Provisional Patent Application No. 62/784,901, entitled "Piezoelectric Pump Adapter For Negative-Pressure Therapy," filed Dec. 26, 2018, which is incorporated herein by reference for all purposes.

TECHNICAL FIELD

The invention set forth in the appended claims relates generally to tissue treatment systems and more particularly, but without limitation, to pump adapters.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes may benefit healthcare providers and patients.

BRIEF SUMMARY

New and useful systems, apparatuses, and methods for adapting a positive pressure pump for negative-pressure therapy are set forth in the appended claims. Illustrative embodiments are also provided to enable a person skilled in the art to make and use the claimed subject matter.

For example, a system for negative-pressure therapy is described. The system can include a dressing configured to be positioned adjacent a tissue site and a piezoelectric pump having at least three inlets and at least one outlet. An adapter can be coupled to the piezoelectric pump and configured to be fluidly coupled to the dressing. The adapter can be configured to aggregate fluid flow into the at least three inlets.

In some embodiments, the adapter can have a block having a first side, a second side opposite the first side, a first end between the first side and the second side, a second end opposite the first end, and a third end perpendicular to and extending from the first end to the second end. A first recess can be disposed in the second side, the first recess depending into the block and having an area less than an area of the second side. A second recess can be disposed in the second side, the second recess depending into the block from the first recess, the second recess having an area less than the area of the first recess. A bore depends through the block from the second recess to the first side, and a conduit can be coupled to the first side. The conduit may have at least one lumen fluidly coupled to the bore. A first projection can extend from the second side and proximate to the first end, the first projection having a length substantially equal to a length of the first end. A second projection can extend from the second side and proximate to the second end, the second projection having a length substantially equal to a length of the second end.

More generally, a fluid aggregator for aggregating fluid flow into an inlet of a piezoelectric pump is described. The fluid aggregator can include a member having a first side, a second side opposite the first side, a first end between the first side and the second side, a second end opposite the first end, and a third end perpendicular to and extending from the first end to the second end. A cavity can be disposed in the second side. The cavity can depend into the member and have an area less than an area of the second side. A channel can be disposed in the second side, the channel can depend into the member from the cavity. The channel can have an area less than the area of the cavity. A fluid lumen can depend through the member from the channel to the first side. A conduit can be coupled to the first side. The conduit can have at least one lumen fluidly coupled to the fluid lumen.

In some embodiments, the second side of the member can be disposed proximate a suction side of the piezoelectric pump. The second side of the member can be coupled to the piezoelectric pump.

Alternatively, other example embodiments may describe a method for manufacturing a fluid aggregator for aggregating fluid flow into an inlet of a piezoelectric pump. A block can be provided. The block can have a first side, a second side opposite the first side, a first end between the first side and the second side, a second end opposite the first end, and a third end perpendicular to and extending from the first end to the second end. A first recess can be formed in the second side. The first recess can depend into the block and have an area less than an area of the second side. A second recess can be formed in the second side. The second recess can depend into the block from the first recess, and the second recess can have an area less than the area of the first recess. A bore can be formed in the block. The bore can depend through the block from the second recess to the first side. A conduit can be coupled to the first side. The conduit can have at least one lumen, and the at least one lumen can be fluidly coupled to the bore. A first projection can be formed. The first projection can extend from the second side and be proximate to the first end. The first projection can have a length substantially equal to a length of the first end. A second projection can be formed. The second projection can extend from the second side and be proximate to the second end. The second projection can have a length substantially equal to a length of the second end.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
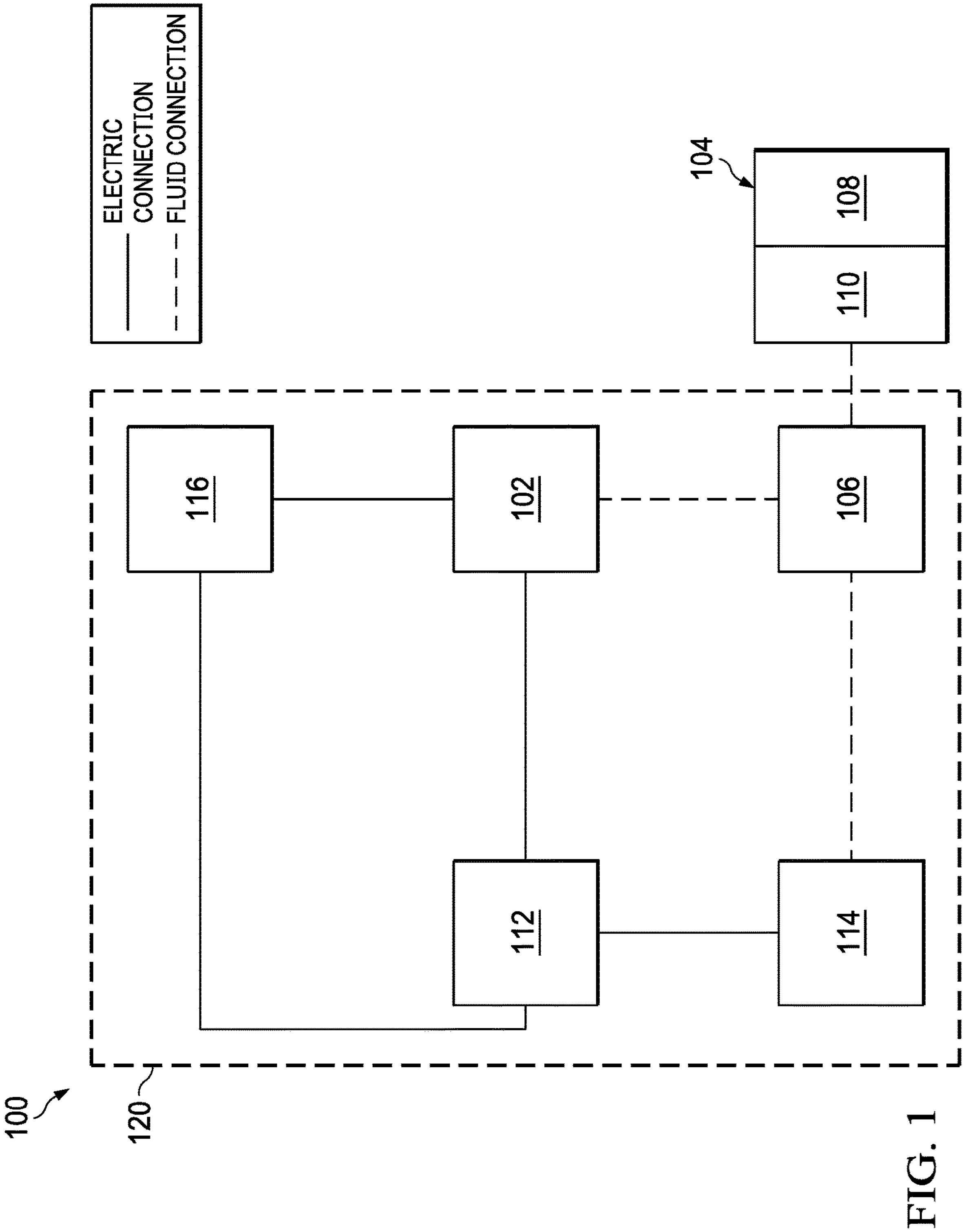
FIG. 1 is a functional block diagram of an example embodiment of a therapy system that can provide negative-pressure treatment in accordance with this specification.

FIG. 1 is a simplified functional block diagram of an example embodiment of a therapy system 100 that can provide negative-pressure therapy to a tissue site in accordance with this specification. The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 102, and one or more distribution components. A distribution component is preferably detachable and may be disposable, reusable, or recyclable. A dressing, such as a dressing 104, and a fluid container, such as a container 106, are examples of distribution components that may be associated with some examples of the therapy system 100. As illustrated in the example of FIG. 1, the dressing 104 may comprise or consist essentially of a tissue interface 108, a cover 110, or both in some embodiments.

A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 104. For example, such a dressing interface may be a SENSA-T.R.A.C.™ Pad available from Kinetic Concepts, Inc. of San Antonio, Texas.

The therapy system 100 may also include a regulator or controller, such as a controller 112. Additionally, the therapy system 100 may include sensors to measure operating parameters and provide feedback signals to the controller 112 indicative of the operating parameters. As illustrated in FIG. 1, for example, the therapy system 100 may include a first sensor 114 and a second sensor 116 coupled to the controller 112.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 102 may be combined with the controller 112 and other components into a therapy unit 120.

In general, components of the therapy system 100 may be coupled directly or indirectly. For example, the negative-pressure source 102 may be directly coupled to the container 106 and may be indirectly coupled to the dressing 104 through the container 106. Coupling may include fluid, mechanical, thermal, electrical, or chemical coupling (such as a chemical bond), or some combination of coupling in some contexts. For example, the negative-pressure source 102 may be electrically coupled to the controller 112 and may be fluidly coupled to one or more distribution components to provide a fluid path to a tissue site. In some embodiments, components may also be coupled by virtue of physical proximity, being integral to a single structure, or being formed from the same piece of material.

A negative-pressure supply, such as the negative-pressure source 102, may be a reservoir of air at a negative pressure or may be a manual or electrically-powered device, such as a vacuum pump, a suction pump, a wall suction port available at many healthcare facilities, or a micro-pump, for example. “Negative pressure” generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 102 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 106 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 112, may be a microprocessor or computer programmed to operate one or more components of the therapy system 100, such as the negative-pressure source 102. In some embodiments, for example, the controller 112 may be a microcontroller, which generally comprises an integrated circuit containing a processor core and a memory programmed to directly or indirectly control one or more operating parameters of the therapy system 100. Operating parameters may include the power applied to the negative-pressure source 102, the pressure generated by the negative-pressure source 102, or the pressure distributed to the tissue interface 108, for example. The controller 112 is also preferably configured to receive one or more input signals, such as a feedback signal, and programmed to modify one or more operating parameters based on the input signals.

Sensors, such as the first sensor 114 and the second sensor 116, are generally known in the art as any apparatus operable to detect or measure a physical phenomenon or property, and generally provide a signal indicative of the phenomenon or property that is detected or measured. For example, the first sensor 114 and the second sensor 116 may be configured to measure one or more operating parameters of the therapy system 100. In some embodiments, the first sensor 114 may be a transducer configured to measure pressure in a pneumatic pathway and convert the measurement to a signal indicative of the pressure measured. In some embodiments, for example, the first sensor 114 may be a piezo-resistive strain gauge. The second sensor 116 may optionally measure operating parameters of the negative-pressure source 102, such as a voltage or current, in some embodiments. Preferably, the signals from the first sensor 114 and the second sensor 116 are suitable as an input signal to the controller 112, but some signal conditioning may be appropriate in some embodiments. For example, the signal may need to be filtered or amplified before it can be processed by the controller 112. Typically, the signal is an electrical signal, but may be represented in other forms, such as an optical signal.

The tissue interface 108 can be generally adapted to partially or fully contact a tissue site. The tissue interface 108 may take many forms, and may have many sizes, shapes, or thicknesses, depending on a variety of factors, such as the type of treatment being implemented or the nature and size of a tissue site. For example, the size and shape of the tissue interface 108 may be adapted to the contours of deep and irregular shaped tissue sites. Any or all of the surfaces of the tissue interface 108 may have an uneven, coarse, or jagged profile.

In some embodiments, the tissue interface 108 may comprise or consist essentially of a manifold. A manifold in this context may comprise or consist essentially of a means for collecting or distributing fluid across the tissue interface 108 under pressure. For example, a manifold may be adapted to receive negative pressure from a negative-pressure source and distribute negative pressure through multiple apertures across the tissue interface 108, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, a manifold may comprise a plurality of pathways, which can be interconnected to improve distribution or collection of fluids. In some illustrative embodiments, a manifold may comprise or consist essentially of a porous material having interconnected fluid pathways. Examples of suitable porous material that can be adapted to form interconnected fluid pathways (e.g., channels) may include cellular foam, including open-cell foam such as reticulated foam; porous tissue collections; and other porous material such as gauze or felted mat that generally include pores, edges, and/or walls. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

In some embodiments, the tissue interface 108 may comprise or consist essentially of reticulated foam having pore sizes and free volume that may vary according to needs of a prescribed therapy. For example, reticulated foam having a free volume of at least 90% may be suitable for many therapy applications, and foam having an average pore size in a range of 400-600 microns (40-50 pores per inch) may be particularly suitable for some types of therapy. The tensile strength of the tissue interface 108 may also vary according to needs of a prescribed therapy. For example, the tensile strength of foam may be increased for instillation of topical treatment solutions. The 25% compression load deflection of the tissue interface 108 may be at least 0.35 pounds per square inch, and the 65% compression load deflection may be at least 0.43 pounds per square inch. In some embodiments, the tensile strength of the tissue interface 108 may be at least 10 pounds per square inch. The tissue interface 108 may have a tear strength of at least 2.5 pounds per inch. In some embodiments, the tissue interface may be foam comprised of polyols such as polyester or polyether, isocyanate such as toluene diisocyanate, and polymerization modifiers such as amines and tin compounds. In some examples, the tissue interface 108 may be reticulated polyurethane foam such as found in GRANUFOAM™ dressing or V.A.C. VERAFLO™ dressing, both available from Kinetic Concepts, Inc. of San Antonio, Texas.

The thickness of the tissue interface 108 may also vary according to needs of a prescribed therapy. For example, the thickness of the tissue interface may be decreased to reduce tension on peripheral tissue. The thickness of the tissue interface 108 can also affect the conformability of the tissue interface 108. In some embodiments, a thickness in a range of about 5 millimeters to 10 millimeters may be suitable.

The tissue interface 108 may be either hydrophobic or hydrophilic. In an example in which the tissue interface 108 may be hydrophilic, the tissue interface 108 may also wick fluid away from a tissue site, while continuing to distribute negative pressure to the tissue site. The wicking properties of the tissue interface 108 may draw fluid away from a tissue site by capillary flow or other wicking mechanisms. An example of a hydrophilic material that may be suitable is a polyvinyl alcohol, open-cell foam such as V.A.C. WHITEFOAM™ dressing available from Kinetic Concepts, Inc. of San Antonio, Texas. Other hydrophilic foams may include those made from polyether. Other foams that may exhibit hydrophilic characteristics include hydrophobic foams that have been treated or coated to provide hydrophilicity.

In some embodiments, the tissue interface 108 may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The tissue interface 108 may further serve as a scaffold for new cell-growth, or a scaffold material may be used in conjunction with the tissue interface 108 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 110 may provide a bacterial barrier and protection from physical trauma. The cover 110 may also be constructed from a material that can reduce evaporative losses and provide a fluid seal between two components or two environments, such as between a therapeutic environment and a local external environment. The cover 110 may comprise or consist of, for example, an elastomeric film or membrane that can provide a seal adequate to maintain a negative pressure at a tissue site for a given negative-pressure source. The cover 110 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the cover 110 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 110 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polymide copolymers. Such materials are commercially available as, for example, Tegaderm® drape, commercially available from 3M Company, Minneapolis Minnesota; polyurethane (PU) drape, commercially available from Avery Dennison Corporation, Pasadena, California; polyether block polyamide copolymer (PEBAX), for example, from Arkema S.A., Colombes, France; and Inspire 2301 and Inpsire 2327 polyurethane films, commercially available from Expopack Advanced Coatings, Wrexham, United Kingdom. In some embodiments, the cover 110 may comprise INSPIRE 2301 having an MVTR (upright cup technique) of 2600 g/m$^2$/24 hours and a thickness of about 30 microns.

An attachment device may be used to attach the cover 110 to an attachment surface, such as undamaged epidermis, a gasket, or another cover. The attachment device may take many forms. For example, an attachment device may be a medically-acceptable, pressure-sensitive adhesive configured to bond the cover 110 to epidermis around a tissue site. In some embodiments, for example, some or all of the cover 110 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

In operation, the tissue interface 108 may be placed within, over, on, or otherwise proximate to a tissue site. If the tissue site is a wound, for example, the tissue interface 108 may partially or completely fill the wound, or it may be placed over the wound. The cover 110 may be placed over the tissue interface 108 and sealed to an attachment surface near a tissue site. For example, the cover 110 may be sealed to undamaged epidermis peripheral to a tissue site. Thus, the dressing 104 can provide a sealed therapeutic environment proximate to a tissue site, substantially isolated from the external environment, and the negative-pressure source 102 can reduce pressure in the sealed therapeutic environment.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies a position in a fluid path relatively closer to a source of negative pressure or further away from a source of positive pressure. Conversely, the term "upstream" implies a position relatively further away from a source of negative pressure or closer to a source of positive pressure.

Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source, and this descriptive convention should not be construed as a limiting convention.

Negative pressure applied across the tissue site through the tissue interface 108 in the sealed therapeutic environment can induce macro-strain and micro-strain in the tissue site. Negative pressure can also remove exudates and other fluids from a tissue site, which can be collected in container 106.

In some embodiments, the controller 112 may receive and process data from one or more sensors, such as the first sensor 114. The controller 112 may also control the operation of one or more components of the therapy system 100 to manage the pressure delivered to the tissue interface 108. In some embodiments, controller 112 may include an input for receiving a desired target pressure and may be programmed for processing data relating to the setting and inputting of the target pressure to be applied to the tissue interface 108. In some example embodiments, the target pressure may be a fixed pressure value set by an operator as the target negative pressure desired for therapy at a tissue site and then provided as input to the controller 112. The target pressure may vary from tissue site to tissue site based on the type of tissue forming a tissue site, the type of injury or wound (if any), the medical condition of the patient, and the preference of the attending physician. After selecting a desired target pressure, the controller 112 can operate the negative-pressure source 102 in one or more control modes based on the target pressure and may receive feedback from one or more sensors to maintain the target pressure at the tissue interface 108.

Negative-pressure therapy has been repeatedly shown to be effective in the treatment of difficult to heal wounds. Unfortunately, some negative-pressure sources generate noise which can dissuade patients from complying with treatment. Some skilled artisans have sought to use piezoelectric pumps to address the noise concerns. A piezoelectric pump may be capable of operation in the high frequency range. As used herein, a high frequency range is a frequency range beyond the range of frequencies detectable by the human ear, e.g., a frequency greater than 16 kilohertz (kHz). Piezoelectric pumps that operate in the high frequency range also generate a significant amount of heat. Maintaining the target pressure level in a negative pressure environment is a demanding application for a piezo-electric pump (positive or negative). To use a piezoelectric pump to generate negative-pressure, the piezoelectric pump may operate continuously or semi-continuously. Continuous or semi-continuous operation of a piezoelectric pump can further exacerbate heat build-up within the piezoelectric pump. Buildup of heat within the piezoelectric pump can degrade the operation of the piezoelectric pump, decreasing the pump life. To date, a negative pressure generating piezo-electric pump suitable for negative-pressure therapy is not commercially available.

Some positive-pressure piezoelectric blowers and pumps are commercially available, but these positive-pressure piezoelectric pumps are often unable to generate and distribute negative pressure at the required duty cycle for negative-pressure therapy. Consequently, a positive-pressure piezoelectric pump may not maintain appropriate negative pressure levels for negative-pressure therapy. Positive-pressure piezoelectric pumps also produce a significant amount of heat that must be dissipated. The heat generated is a result of the decreased efficiency of the piezoelectric pump compared to a diaphragm pump. Positive pressure generating piezo-electric pumps designed for blood pressure checks have been developed but these are only used intermittently as it fills the blood pressure cuff and then is switched off so it has a chance to cool down. Positive pressure piezoelectric pumps may be used to generate negative pressure but dissipating heat as the flow of the pump is adapted for negative pressure has proven difficult, preventing the positive-pressure piezoelectric pump from being able to keep up with the required demand. For example, one positive-pressure piezoelectric pump may consume approximately 0.9 Watts when running in vacuum mode with approximately 100 cubic centimeters per minute (cc/min) of fluid flow at 125 mmHg. If the heat is not dissipated from the positive-pressure piezoelectric pump, the pump may begin to audibly whine. For some piezoelectric pumps, if the piezoelectric pump rises above a temperature of 60° C., the piezoelectric pump will whine, and its ability to move fluid through the pump will degrade. Consequently, a positive-pressure piezoelectric pump may not have a life-cycle that is long enough to be used in a negative-pressure therapy environment. Persons skilled in the art have long sought a silent, low-profile negative-pressure source to enable wearable negative-pressure therapy systems. A piezoelectric pump capable of generating negative pressure for the purpose of providing negative-pressure therapy while addressing the need to dissipate heat and operate outside the range of human hearing could address a long-felt need in the art.

Figure 2:
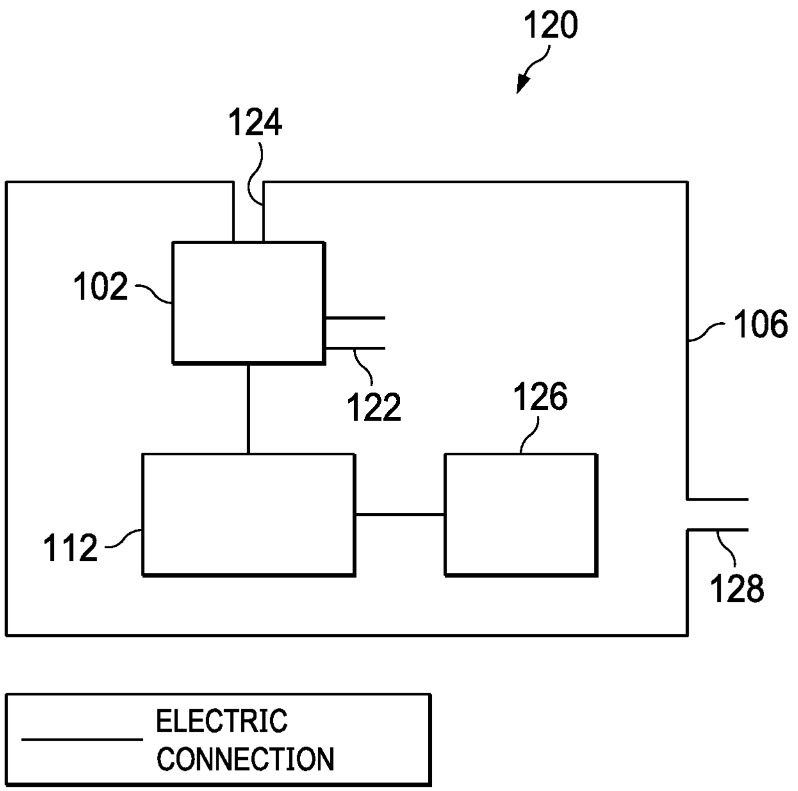
FIG. 2 is a schematic diagram illustrating additional details of a therapy unit that can be used with some embodiments of the therapy system of FIG. 1.

FIG. 2 is a schematic diagram illustrating additional details of the therapy unit 120 of FIG. 1. In some embodiments, the therapy unit 120 can include the negative-pressure source 102, the container 106, and the controller 112. The therapy unit 120 can provide a negative pressure using a positive-pressure piezoelectric pump. The therapy unit 120 can also act as a conduit to transmit and thermally conduct heat away from the positive pressure pump. In some embodiments, a positive-pressure piezoelectric pump can be operated to generate negative pressure without interfering with the operation of or modifying the positive-pressure piezoelectric pump.

The container 106 may have a fluid inlet 128. The fluid inlet 128 may be a fluid coupling permitting fluid communication from an external device to an interior of the container 106. For example, the dressing 104 may be coupled to the fluid inlet 128, or a fluid conductor may be coupled to the fluid inlet 128.

In some embodiments, the negative-pressure source 102 may be disposed in the container 106. The negative-pressure source 102 may have an inlet 122 and an outlet 124. The inlet 122 may be a suction side of the negative-pressure source 102. A side of a negative-pressure source, such as a pump, can refer to the portion of the pump operating to draw fluid into the pump or the portion of the pump operating to move fluid out of the pump. Generally, an impeller or diaphragm may separate the sides of a pump, operating both to move fluid into and out of the pump. A suction side can generally refer to the side of the pump operating to draw fluid into the pump and is generally at a pressure that is less than atmospheric pressure. A discharge side can generally refer to the side of the pump operating to move fluid out of the pump and is generally at a pressure that is greater than atmospheric pressure. The inlet 122 may provide a fluid inlet into the negative-pressure source 102. In some embodiments, the inlet 122 may be open to an interior of the container 106. For example, fluid may flow into the negative-pressure source 102 from the container 106 through the inlet 122. The outlet 124 may be a discharge side of the negative-pressure source 102. In some embodiments, the outlet 124 may be fluidly coupled to the ambient environment. For example, the outlet 124 may be fluidly coupled by a fluid conductor to a vent of the container 106. Fluid may flow out of the container 106 through the outlet 124 of the negative-pressure source 102.

The controller 112 can be disposed in the container 106. For example, the controller 112 can be disposed in the container 106 and electrically coupled to the negative-pressure source 102. A battery 126 can also be disposed in the container 106. The battery 126 may be electrically coupled to the controller 112. The controller 112 may control current between the battery 126 and the negative-pressure source 102. In some embodiments, the controller 112 can control the operating state, speed, and throughput of the negative-pressure source 102 by controlling the supply of current from the battery 126.

Figure 3:
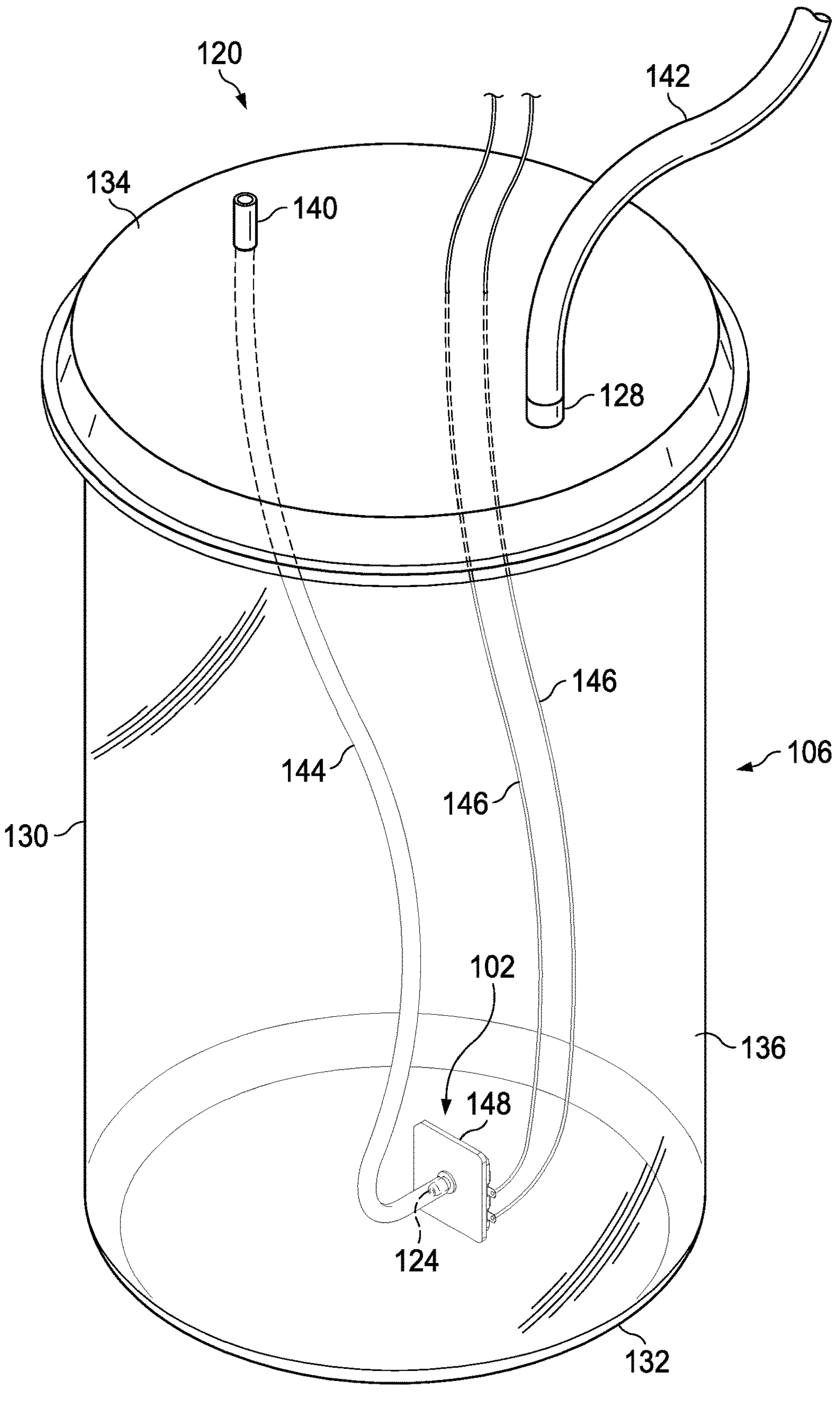
FIG. 3 is a perspective view illustrating additional details that may be associated with some embodiments of the therapy unit of FIG. 2.

FIG. 3 is a perspective view illustrating additional details of the therapy unit 120 of FIG. 2. The therapy unit 120 of FIG. 3 includes the container 106 and the negative-pressure source 102. The container 106 may have an annular wall 130, a closed end 132, and an open end enclosed by a lid 134. The lid 134 may be removable. The annular wall 130 and the closed end 132 can form an interior 136. The interior 136 can be an open cavity. The interior 136 may receive fluids or other materials for storage within the container 106. In some embodiments, a fluid solidifier, such as an absorbent, desiccant, or other device can be disposed within the interior 136. The fluid solidifier may interact with liquids disposed within the container 106 to trap and contain the liquids.

The lid 134 may be removably coupled to the open end of the container 106. The lid 134 may have the fluid inlet 128 and a fluid outlet 140. The fluid inlet 128 and the fluid outlet 140 may provide fluid communication across the lid 134 with the interior 136 of the container 106. In some embodiments, the fluid inlet 128 may be coupled to a conduit 142. The conduit 142 can have one or more lumens. The conduit 142 can be a fluid conductor operable to fluidly couple two or more components for the conveyance of fluid therebetween. For example, the conduit 142 can fluidly couple the fluid inlet 128 to another device, such as the dressing 104. The fluid outlet 140 can be a vent or other fluid conductor permitting fluid communication across the lid 134. In some embodiments, a filter, such as an antimicrobial or odor filter can be disposed in the fluid outlet 140.

The negative-pressure source 102 can be a pump 148 and can be disposed in the interior 136. The pump 148 can be loosely disposed in the interior 136. In other embodiments, the pump 148 can be secured to the container 106, for example, to the lid 134. The pump 148 can include the inlet 122 (not shown) and the outlet 124. A conduit 144 may fluidly couple the outlet 124 to the fluid outlet 140 of the lid 134. The inlet 122 may be open to the interior 136. The pump 148 can be electrically coupled to the controller 112 (not shown) and the battery 126 (not shown). In some embodiments, the controller 112 and the battery 126 can be located externally to the container 106 and one or more wires 146 can couple the pump 148 to the controller 112 and the battery 126 through the lid 134. In other embodiments, the controller 112 and the battery 126 can be disposed in the interior 136, for example, by being coupled to the lid 134.

The pump 148 may also be a diaphragm pump. A diaphragm pump is a type of positive displacement pump that can move fluid using the reciprocating action of a diaphragm or membrane. The diaphragm can form a portion of a pump chamber. The diaphragm can be displaced, causing the volume of the pump chamber to change. For example, the diaphragm can be sealed at its periphery to the pump chamber, and a center of the diaphragm can be pushed into the pump chamber. This action can cause the pump chamber to decrease in volume as the diaphragm depends into the pump chamber. As the volume of the pump chamber decreases, the pressure in the pump chamber increases, forcing fluid out of the pump chamber through a one-way valve. If the diaphragm is relaxed and returns to the original position of the diaphragm, the pump chamber volume can increase. Increasing the volume of the pump chamber can cause the pressure in the pump chamber to decrease, drawing fluid into the pump chamber through another one-way valve. The diaphragm can be cyclically flexed, causing repeated movement of fluid out of and into the pump chamber and generating flow through the pump 148.

In some embodiments, the diaphragm can be coupled to a piezoelectric actuator or be formed from a piezoelectric material. A piezoelectric material is a material that can accumulate an electric charge in response to a mechanical stress. Application of a voltage to the piezoelectric material can cause a corresponding mechanical reaction in the material. A piezoelectric diaphragm pump uses the mechanical/electric relationship in a piezoelectric material to cyclically displace the diaphragm in response to a sine wave voltage applied to the piezoelectric material.

In operation, the pump 148 can be actuated, causing the pump 148 to draw fluid from the interior 136 into the pump 148 through the inlet 122. The pump 148 can force the fluid drawn from the interior 136 out of the container 106 through the conduit 144 and the fluid outlet 140. The movement of fluid from the interior 136 through the pump 148 and out of the container 106 can develop a negative pressure in the interior 136, allowing the interior 136 to function as a negative-pressure plenum. As a negative pressure is developed in the interior 136, fluid may flow into the interior 136 through the fluid inlet 128 and the conduit 142. The fluid drawn into the interior 136 through the fluid inlet 128 may be from a device fluidly coupled to the fluid inlet 128 by the conduit 142. For example, if the conduit 142 is fluidly coupled to the dressing 104, the development of a negative pressure in the interior 136 by the pump 148 may draw fluid into the interior 136 through the fluid inlet 128 from the dressing 104. As a result, a negative-pressure may be developed in a sealed therapeutic environment formed by the dressing 104. By developing negative pressure in the interior 136, delivery of negative pressure through the fluid inlet 128 can be smoothed out. For example, the interior 136 may function as a plenum from which negative pressure can be distributed to another device. As negative-pressure is distributed from the interior 136, devices fluidly coupled upstream of the interior 136 may be shielded from pressure pulsations that may occur at the inlet 122 of the pump 148. Heat generated by the pump 148 can be dissipated through the volume of the interior 136 of the container 106 by radiative and convective action.

In some embodiments, the negative-pressure source 102, the controller 112, and the battery 126 can be positioned in the container 106 free from liquids in the container 106. For example, the controller 112, and the battery 126 can be coupled to the lid 134 so that the inlet 122 can be in fluid communication with the interior 136 of the container 106 while being free from liquids that may be drawn into the interior 136 of the container 106.

Figure 4:
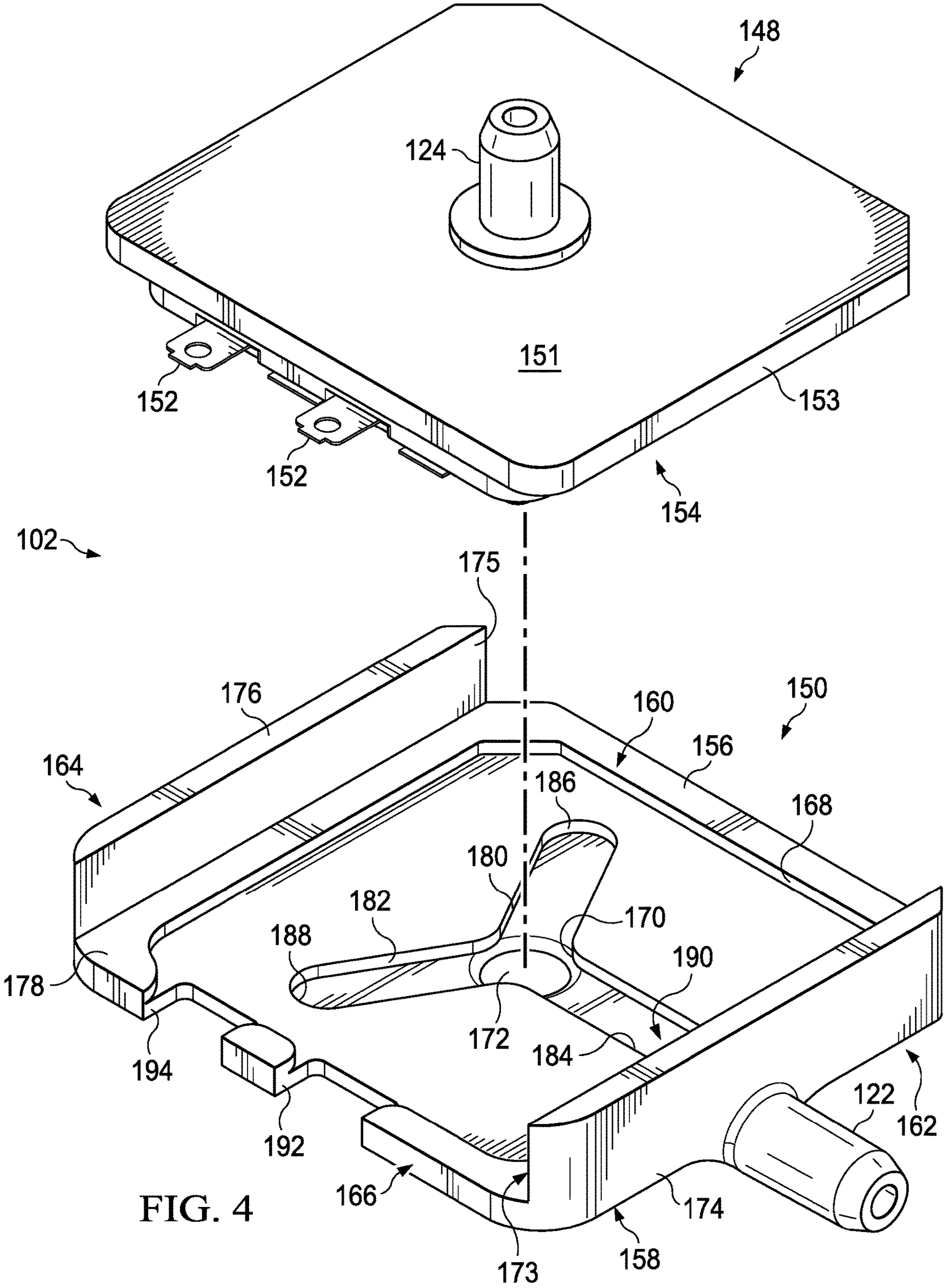
FIG. 4 is a perspective assembly view illustrating additional details that may be associated with another therapy device that may be used with the therapy system of FIG. 1.

FIG. 4 is a perspective assembly view illustrating additional details that may be associated with some embodiments of the negative-pressure source 102 of FIG. 1. The negative-pressure source 102 may include the pump 148 and a fluid aggregator, such as an adapter 150. The pump 148 may include the outlet 124 and the one or more electric contacts 152. The pump 148 may have a discharge side having a discharge plate 151 with the outlet 124 disposed on the discharge plate 151. The outlet 124 may provide fluid communication across the discharge plate 151 with the pump chamber of the pump 148. The electric contacts 152 can be coupled to the controller 112 and a voltage source such as the battery 126 to control operation of the diaphragm of the pump 148. The pump 148 can also have the suction side 154. In some embodiments, the pump 148 can have an edge surface 153. The edge surface 153 can form a side wall, such as an outer side wall(s), of the pump 148. The edge surface 153 can extend from the discharge plate 151 to the suction side 154. In some embodiments, the edge surface 153 can circumscribe the pump 148.

In some embodiments, the adapter 150 can cover a fluid inlet of the pump 148 and translate an open area of the suction side 154 of the pump 148 into a vacuum port or horizontal spigot, such as the inlet 122. The adapter 150 can be coupled to and seal to the suction side 154 of the pump 148 without interfering with the operation of the pump 148. The adapter 150 may have a member, such as a block 156 having a first side 158 and a second side 160. The adapter 150 may have a first end 162 extending between the first side 158 and the second side 160 and a second end 164 opposite the first end 162. The adapter may have a third end 166 perpendicular to and extending from the first end 162 to the second end 164. In some embodiments, the adapter 150 can have a peripheral shape that matches a shape of the edge surface 153. In other embodiments, the peripheral shape of the adapter 150 may not match the edge surface 153.

In some embodiments, the adapter 150 may have cavity, such as a first recess 168, disposed in the second side 160 and depending into the block 156. The first recess 168 may have an area less than an area of the second side 160. In some embodiments, the first recess 168 may be sized to receive the suction side 154 of the pump 148. For example, the first recess 168 may have an area and a shape such that at least a portion of the suction side 154 of the pump 148 can be received by the first recess 168 without interfering with the operation of the pump 148. In some embodiments, the first recess 168 may be substantially square and form a shoulder 178. The shoulder 178 may substantially surround the first recess 168. The shoulder 178 may extend from an edge of the block 156 to the first recess 168.

The adapter 150 may have a channel, such as a second recess 170 disposed in the first recess 168 and depending into the block 156. The second recess 170 may have an area less than the area of the first recess 168. In some embodiments, the second recess 170 may be disposed near a center of the first recess 168. The second recess 170 may be T-shaped, V-shaped, Y-shaped, circular, square, triangular, or amorphous shaped. The second recess 170 may have a first arm 180, a second arm 182, and a third arm 184. Each of the first arm 180, the second arm 182, and the third arm 184 may have a first end and a second end 186, 188, 190, respectively. The first end of each of the first arm 180, the second arm 182, and the third arm 184 may be positioned proximate to a center of the block 156. The second end 186, 188, 190 of the first arm 180, the second arm 182, and the third arm 184, respectively, may be spaced from the center of the block 156. In some embodiments, the first arm 180, the second arm 182, and the third arm 184 may have a same length between the first end and the second end. In other embodiments, the first arm 180, the second arm 182, and the third arm 184 may have different lengths. In some embodiments, the second end 186, the second end 188, and the second end 190 may be equidistantly spaced from each other. In other embodiments, the second end 186, the second end 188, and the second end 190 may not be equidistantly spaced from each other. The second end 186, the second end 188, and the second end 190 may be rounded. In other embodiments, the second end 186, the second end 188, and the second end 190 may be square, triangular, or amorphous shaped.

A fluid lumen such as a bore 172 may depend into and through the block 156. In some embodiments, the bore 172 may be located proximate to the center of the block 156. The bore 172 may provide fluid communication across the block 156 from the first side 158 to the second side 160. The bore 172 may be positioned in the second recess 170 and have a chamfered transition from the bore 172 to the second recess 170. For example, the bore 172 may intersect a surface of the second recess 170 to form an edge, and the edge can be chamfered. In some embodiments, the first ends of each of the first arm 180, the second arm 182, and the third arm 184 may be positioned over the bore 172.

The adapter 150 may have a first leg or a first projection 174 extending from the second side 160 proximate to the first end 162. The first projection 174 may have a length substantially equal to a length of the first end 162. The first projection 174 may have a height substantially equal to a depth of the pump 148. The first projection 174 may have a first surface 173. The first surface 173 may face the first recess 168 and extend from the shoulder 178 to a height of the first projection 174. The adapter 150 may have a second leg or second projection 176 extending from the second side 160 proximate to the second end 164. The second projection 176 may have a length substantially equal to a length of the second end 164. The second projection may have a height substantially equal to a depth of the pump 148. The second projection 176 may have a second surface 175. The second surface 175 may face the first recess 168 and the first surface 173. The second surface 175 may extend from the shoulder 178 to a height of the second projection 176. The first projection 174 and the second projection 176 may be sized to provide an area for secure attachment of the adapter 150 to the pump 148.

The adapter 150 may have a first notch 192 extending into the third end 166 of the block 156. The first notch 192 may extend into the first recess 168 through the shoulder 178. The first notch 192 may have a depth substantially equal to a depth of the block 156. The adapter 150 may have a second notch 194 extending into the third end 166 of the block 156. The second notch 194 may extend into the first recess 168 through the shoulder 178. The second notch 194 may have a depth substantially equal to a depth of the block 156. The second notch 194 may be proximate to the second projection 176, and the first notch 192 may be proximate to the second notch 194. The first notch 192 and the second notch 194 may be closer to the second projection 176 than to the first projection 174. In some embodiments, the first notch 192 and the second notch 194 can be positioned to receive the electric contacts 152.

Figure 5:
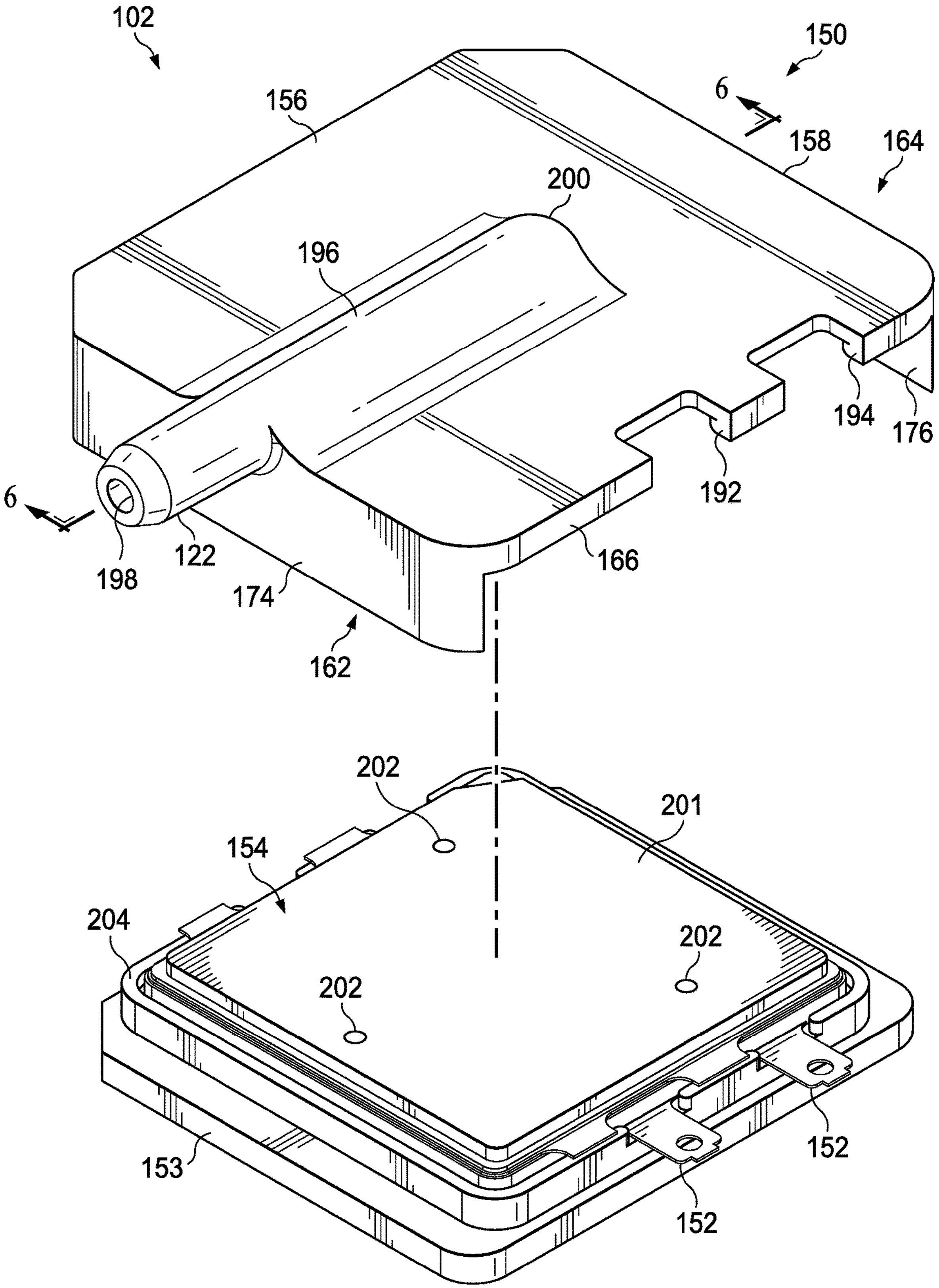
FIG. 5 is a perspective assembly view illustrating additional details that may be associated with the therapy device of FIG. 4.

FIG. 5 is a perspective assembly view illustrating additional details that may be associated with some embodiments of the negative-pressure source 102. A conduit 196 may be coupled to the first side 158 of the block 156. The conduit 196 may have a lumen 198 extending through the conduit 196. A first end 200 of the conduit 196 may be disposed over the center of the block 156. A second end of the conduit 196 may have the inlet 122. The inlet 122 may project from the block 156. In some embodiments, the inlet 122 may be perpendicular to the first end 162. In some embodiments, the conduit 196 may have a side that tapers from the conduit 196 into the first side 158 of the block 156. In some embodiments, the inlet 122 comprises a frusto-conical end of the conduit 196. The inlet 122 may be a tube connector capable of being coupled to a fluid conductor or other device.

In some embodiments, the pump 148 can have an inlet plate 201 having at least one inlet. For example, the at least one inlet of the inlet plate 201 can be a plurality of inlets 202. The inlet plate 201 can form a portion of the suction side 154 of the pump 148. The inlet plate 201 may be opposite the discharge plate 151. In some embodiments, the inlet plate 201 and the discharge plate 151 can form at least a portion of an exterior of the pump 148. The inlets 202 can be openings in the inlet plate 201 providing fluid communication across the inlet plate 201 with a pump chamber of the pump 148. In some embodiments, at least three inlets 202 can be disposed in the inlet plate 201. In some embodiments, the inlets 202 may be spaced apart from each other. For example, the inlets 202 may be equidistantly spaced from each other in the inlet plate 201. In other embodiments, the inlets 202 may not be spaced apart from each other. The inlets 202 may be in fluid communication with the pump chamber of the pump 148. In some embodiments, the inlet plate 201 of the pump 148 may be a heat sink. For example, the inlet plate 201 may be formed from copper and conduct heat generated by operation of the pump 148 into the ambient environment. The inlet plate 201 can collect heat from the pump 148 and dissipate the heat into the ambient environment of the pump 148. In some embodiments, the pump 148 may include a mounting shoulder 204 positioned between the inlet plate 201 and the edge surface 153. In some embodiments, the mounting shoulder 204 can circumscribe the inlet plate 201. The mounting shoulder 204 may be vertically displaced relative to the inlet plate 201.

Figure 6:
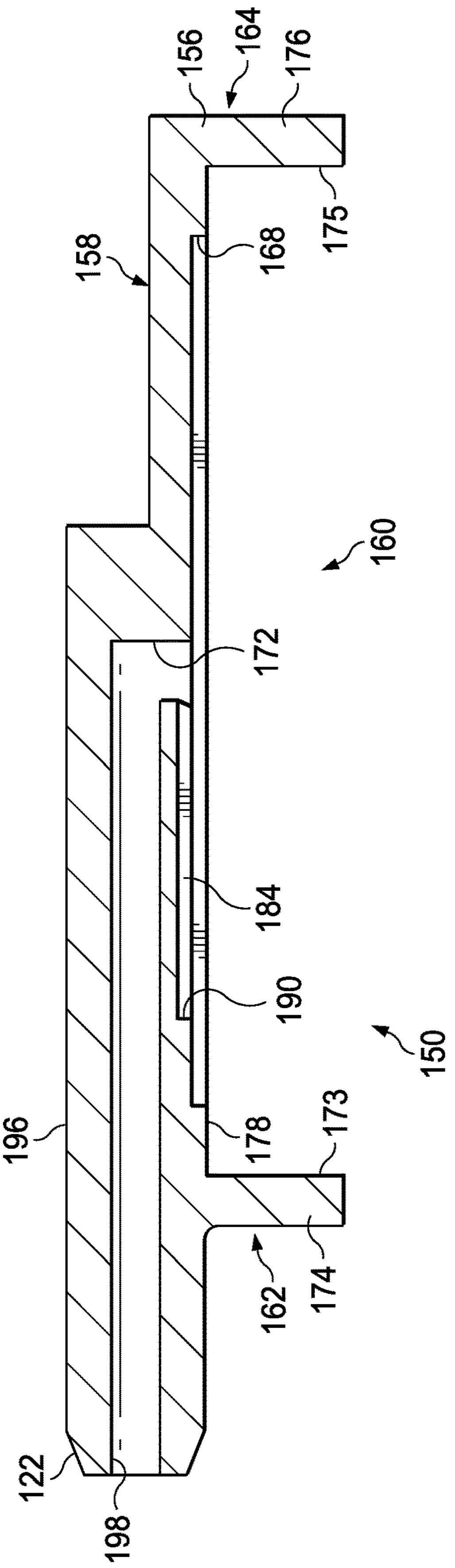
FIG. 6 is a sectional view taken along line 6-6 of FIG. 5 illustrating additional details that may be associated with an adapter of the therapy device of FIG. 4.

FIG. 6 is a sectional view illustrating additional details of the adapter 150 taken along line 6-6 of FIG. 5. In some embodiments, the lumen 198 is in fluid communication with the bore 172. Fluid communication from the first side 158 to the second side 160 may occur through the lumen 198, the bore 172, and the third arm 184 of the second recess 170. The second recess 170 can create a channel for the dissipation of heat generated by the pump 148. The bore 172 can be offset from the inlets 202. The bore 172 may not be positioned adjacent to an individual inlet 202 of the plurality of inlets 202.

Figure 7:
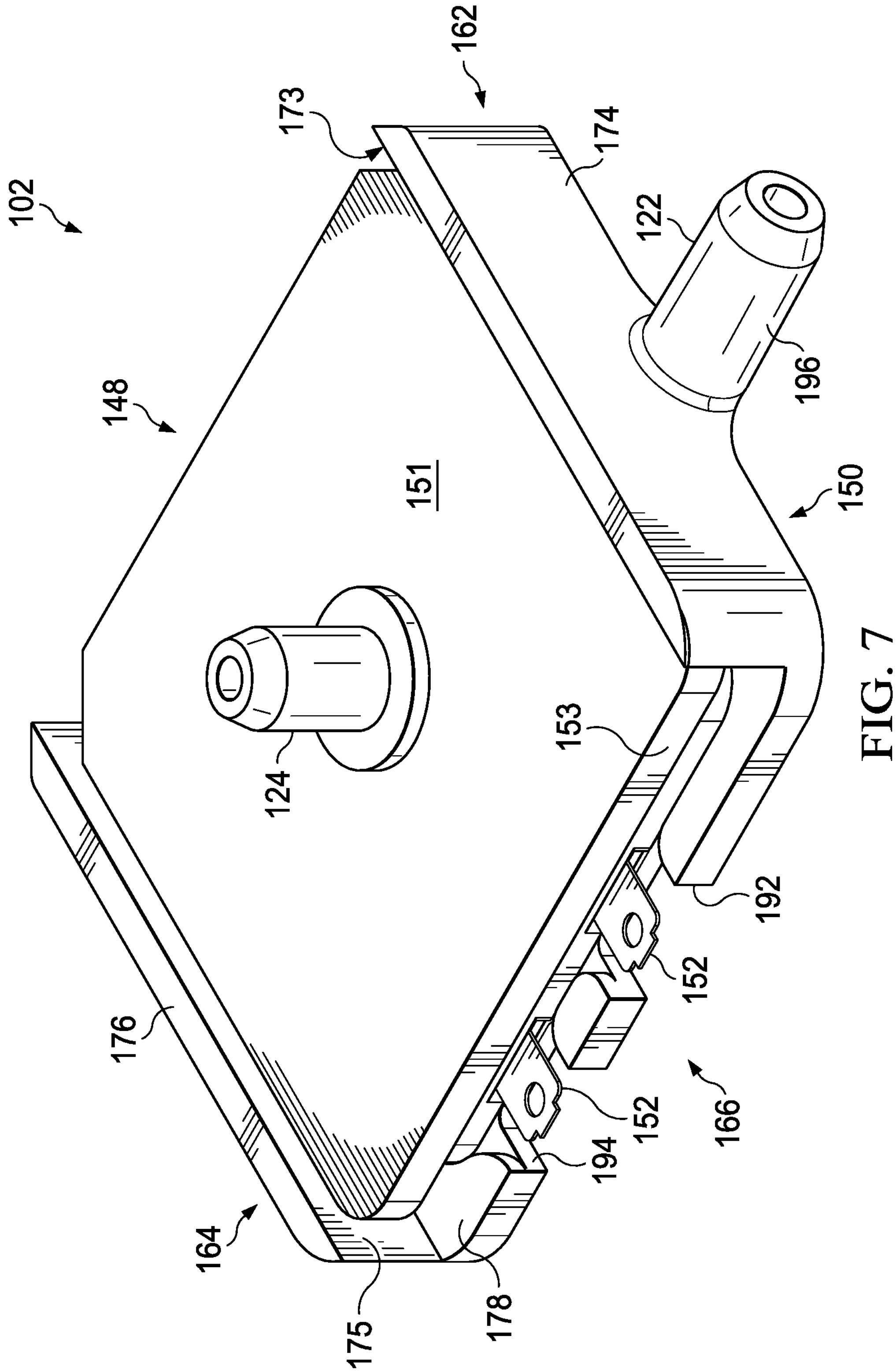
FIG. 7 is a top perspective view illustrating additional details that may be associated with the therapy device of FIG. 4.
Figure 8:
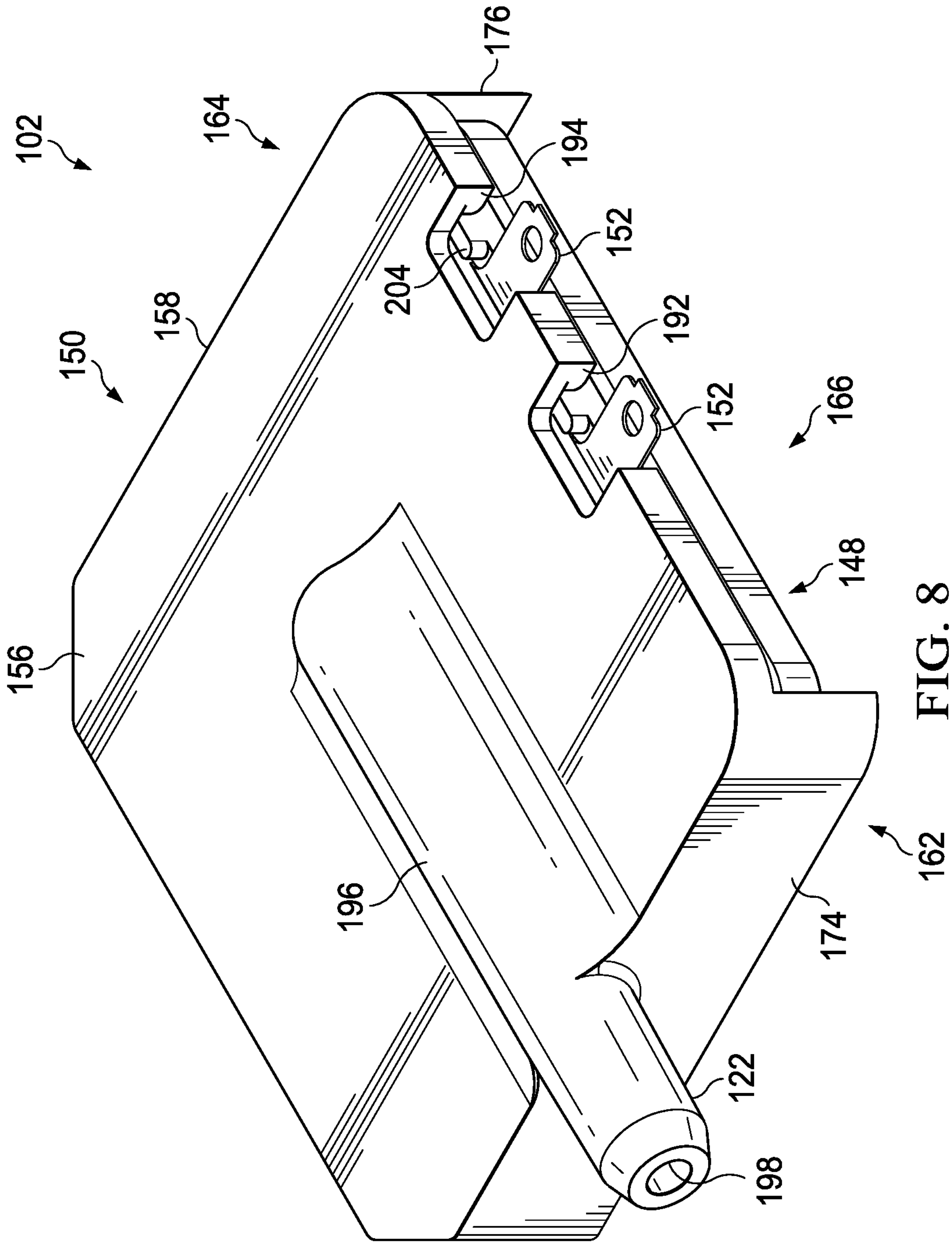
FIG. 8 is a bottom perspective view illustrating additional details that may be associated with the therapy device of FIG. 4.

FIG. 7 is a top perspective view and FIG. 8 is a bottom perspective view of the negative-pressure source 102 illustrating additional details that may be associated with some embodiments. The adapter 150 and the pump 148 may be coupled to each other. In some embodiments, the electric contacts 152 may be aligned with the first notch 192 and the second notch 194. The pump 148 can be placed between the first projection 174 and the second projection 176 so that the inlet plate 201 of the pump 148 is adjacent to the first recess 168. In some embodiments, at least a portion of the inlet plate 201 can fit into the first recess 168. The inlets 202 may be disposed over the first arm 180, the second arm 182, and the third arm 184 of the second recess 170. At least one inlet 202 may be proximate to the second end 186, the second end 188, and the second end 190 of the first arm 180, the second arm 182, and the third arm 184, respectively. The adapter 150 covers the inlet plate 201 having the inlets 202, translating the open area into the channel of the second recess 170, the bore 172, the lumen 198, and the inlet 122.

The adapter 150 seals to the inlet plate 201 without contacting the functioning components of the pump 148. For example, the inlet plate 201 can be positioned in the first recess 168 so that the mounting shoulder 204 is adjacent to the shoulder 178. In some embodiments, the first recess 168 may have a depth greater than a distance between the mounting shoulder 204 and a surface of the inlet plate 201. If the mounting shoulder 204 contacts the shoulder 178, a gap may be formed between an interior surface of the first recess 168 and the surface of the inlet plate 201. In other embodiments, no gap may be formed between the interior surface of the first recess 168 and the surface of the inlet plate 201. The mounting shoulder 204 can be coupled to the shoulder 178 of the adapter 150, securing the adapter 150 to the pump 148. In other embodiments, the edge surface 153 can be coupled to the first surface 173 and the second surface 175 to secure the adapter 150 to the pump 148.

In operation, the pump 148 can be actuated by applying an electrical current to the electric contacts 152. In response, fluid can be drawn through the lumen 198 into the bore 172, the second recess 170, and the inlets 202. The adapter 150 can aggregate fluid flow into the inlets 202 by directing fluid flow from the lumen 198 through the second recess 170 and across the inlet plate 201. Movement of fluid through the second recess 170 into the inlets 202 moves fluid across the inlet plate 201 of the suction side 154 of the pump 148. Movement of fluid across the inlet plate 201 of the pump 148 through the second recess 170 can dissipate heat generated by the pump 148 using convective cooling. Additional heat dissipation can be achieved through conductive heat transfer between the first surface 173, the second surface 175, the first recess 168, and the shoulder 178 of the adapter 150 and the edge surface 153 and the suction side 154 of the pump 148.

Figure 9:
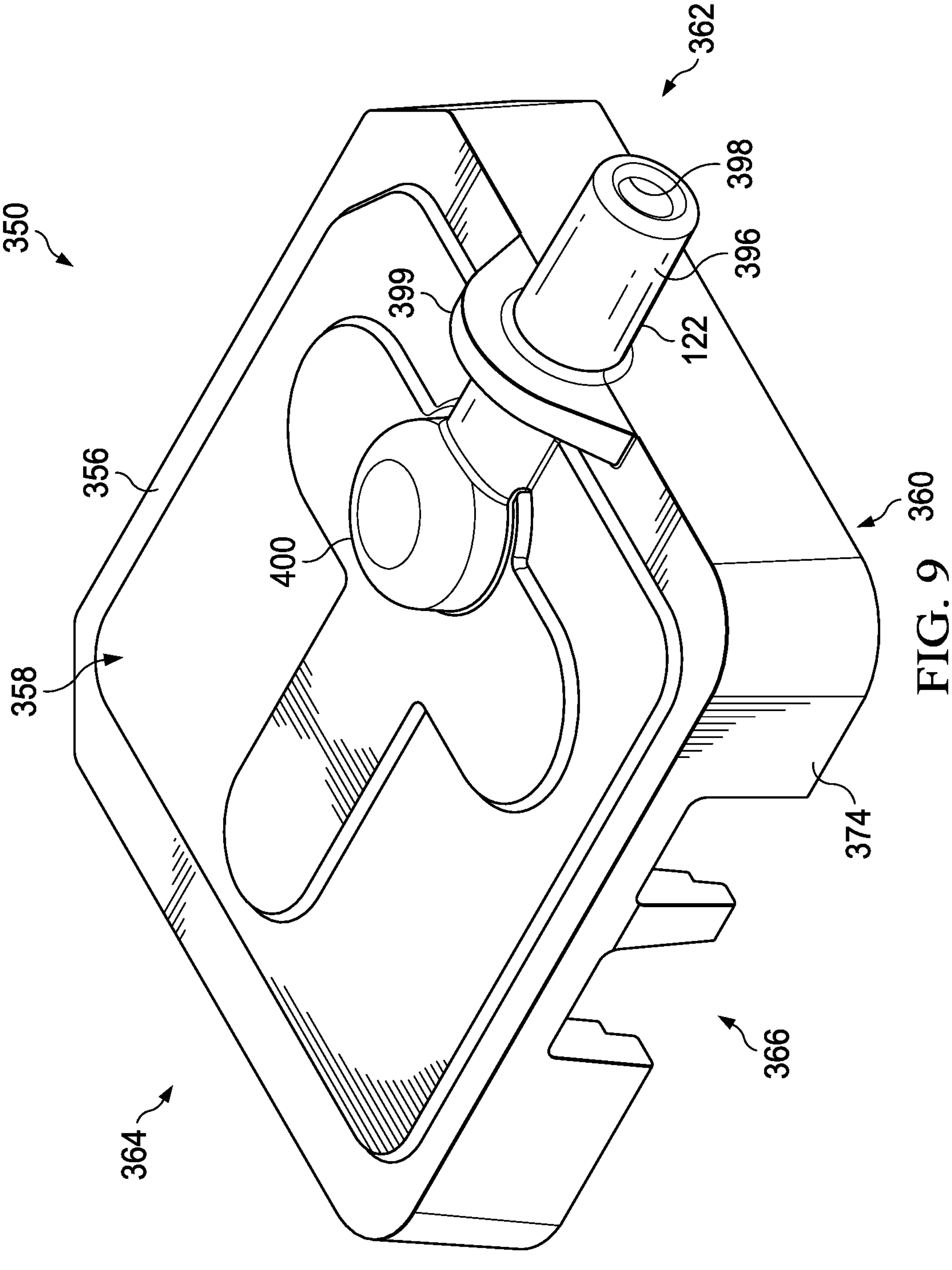
FIG. 9 is a perspective view illustrating additional details that may associated with another adapter of a therapy device that may be used with the therapy system of FIG. 1.

FIG. 9 is a perspective view illustrating additional details of another fluid aggregator that may be used in some embodiments of the therapy system of FIG. 1. The fluid aggregator may be an adapter 350 and can be coupled to the pump 148. In some embodiments, the adapter 350 can cover a fluid inlet of the pump 148 and translate an open area of the suction side 154 of the pump 148 into a vacuum port, such as the inlet 122. The adapter 350 can be coupled to and seal to the suction side 154 of the pump 148 without interfering with the operation of the pump 148. The adapter 350 may have a member, such as a block 356 having a first side 358 and a second side 360. The adapter 350 may have a first end 362 extending between the first side 358 and the second side 360 and a second end 364 opposite the first end 362. The adapter 350 may have a third end 366 perpendicular to and extending from the first end 362 to the second end 364. In some embodiments, the adapter 350 can have a peripheral shape that matches a shape of the edge surface 153. In other embodiments, the peripheral shape of the adapter 350 may not match the edge surface 153.

A conduit 396 may be coupled to the first side 358 of the block 356. The conduit 396 may have a lumen 398 extending through the conduit 396. A first end 400 of the conduit 396 may be disposed over the center of the block 356. A second end of the conduit 396 may have the inlet 122. The inlet 122 may project from the block 356. In some embodiments, the inlet 122 may be perpendicular to the first end 362. In some embodiments, the conduit 396 may have a side that tapers from the conduit 396 into the first side 358 of the block 356. In some embodiments, the inlet 122 comprises a frusto-conical end of the conduit 396. The inlet 122 may be a tube connector capable of being coupled to a fluid conductor or other device. A vertical support 399 can be coupled to the first side 358 of the adapter 350 proximate to the first end 362. The conduit 396 may pass through the vertical support 399. The vertical support 399 can provide a stop, preventing the conduit 396 from being inserted into another conduit past the position of the vertical support 399.

Figure 10:
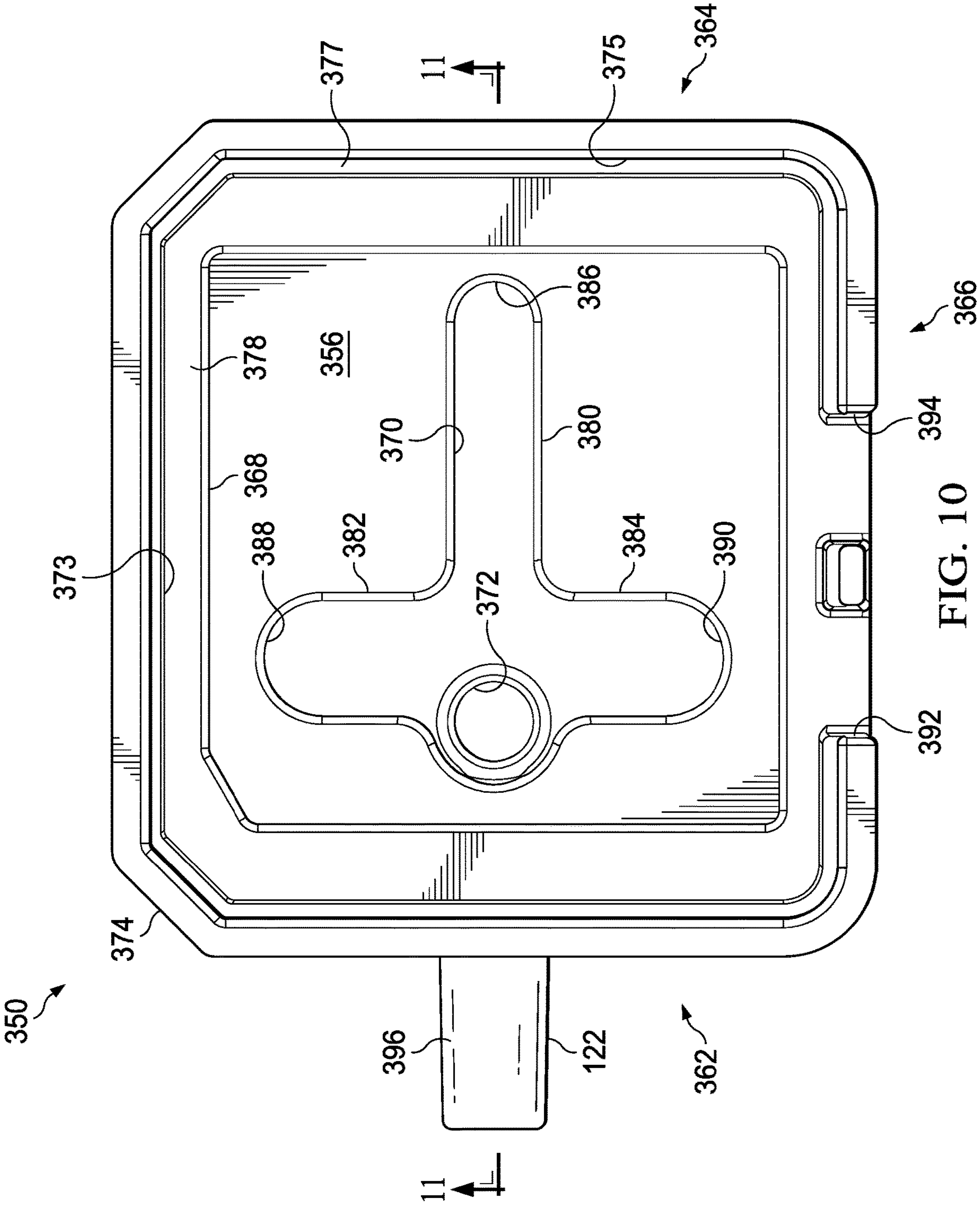
FIG. 10 is a bottom plan view illustrating additional details that may be associated with the adapter of FIG. 9.

FIG. 10 is a plan view illustrating additional details that may be associated with some embodiments of the adapter 350. In some embodiments, the adapter 350 may have cavity, such as a first recess 368, disposed in the second side 360 and depending into the block 356. The first recess 368 may have an area less than an area of the second side 360. In some embodiments, the first recess 368 may be sized to receive the suction side 154 of the pump 148. For example, the first recess 368 may have an area and a shape such that at least a portion of the suction side 154 of the pump 148 can be received by the first recess 368 without interfering with the operation of the pump 148. In some embodiments, the first recess 368 may be substantially square and form a shoulder 378. The shoulder 378 may substantially surround the first recess 368. The shoulder 378 may extend from an edge of the block 356 to the first recess 368.

The adapter 350 may have a channel, such as a second recess 370 disposed in the first recess 368 and depending into the block 356. The second recess 370 may have an area less than the area of the first recess 368. In some embodiments, the second recess 370 may be disposed near a center of the first recess 368. The second recess 370 may be T-shaped, V-shaped, Y-shaped, circular, square, triangular, or amorphous shaped. The second recess 370 may have a first arm 380, a second arm 382, and a third arm 384. Each of the first arm 380, the second arm 382, and the third arm 384 may have a first end and a second end 386, 388, 390, respectively. The first end of each of the first arm 380, the second arm 382, and the third arm 384 may be positioned proximate to a center of the block 356. The second end 386, 388, 390 of the first arm 380, the second arm 382, and the third arm 384, respectively, may be spaced from the center of the block 356. In some embodiments, the first arm 380, the second arm 382, and the third arm 384 may have a same length between the first end and the second end. In other embodiments, the first arm 380, the second arm 382, and the third arm 384 may have different lengths. In some embodiments, the second end 386, the second end 388, and the second end 390 may be equidistantly spaced from each other. In other embodiments, the second end 386, the second end 388, and the second end 390 may not be equidistantly spaced from each other. The second end 386, the second end 388, and the second end 390 may be rounded. In other embodiments, the second end 386, the second end 388, and the second end 390 may be square, triangular, or amorphous shaped.

A fluid lumen such as a bore 372 may depend into and through the block 356. In some embodiments, the bore 372 may be located proximate to the center of the block 356. The bore 372 may provide fluid communication across the block 356 from the first side 358 to the second side 360. The bore 372 may be positioned in the second recess 370 and have a chamfered transition from the bore 372 to the second recess 370. For example, the bore 372 may intersect a surface of the second recess 370 to form an edge, and the edge can be chamfered. In some embodiments, the first ends of each of the first arm 380, the second arm 382, and the third arm 384 may be positioned over the bore 372.

The adapter 350 may have an annular wall 374 extending from the second side 360. The annular wall 374 may be disposed at a periphery of the block 356. The annular wall 374 may have a height substantially equal to a depth of the pump 148. The annular wall 374 may have an interior surface 373. The interior surface 373 may face the first recess 368 and extend from the shoulder 378 to a height of the annular wall 374. The annular wall 374 may be sized to provide an area for secure attachment of the adapter 350 to the pump 148. In some embodiments, a wall recess 375 may be formed in the annular wall 374. The wall recess 375 may depend into the annular wall 374 from an end of the annular wall 374 opposite the shoulder 378. The wall recess 375 may be proximate to the interior surface 373 and form an annular shoulder 377 having a width less than a width of the annular wall 374.

The adapter 350 may have a first notch 392 extending through the annular wall 374. The adapter 350 may have a second notch 394 extending through the annular wall 374. The second notch 394 may extend into the first recess 368 through the shoulder 378. The first notch 392 and the second notch 394 may have a depth substantially equal to a height of the annular wall 374. The first notch 392 may be proximate to the first end 362, and the second notch 394 may be proximate to the second end 364. In some embodiments, the first notch 392 and the second notch 394 can be positioned to receive the electric contacts 152.

Figure 11:
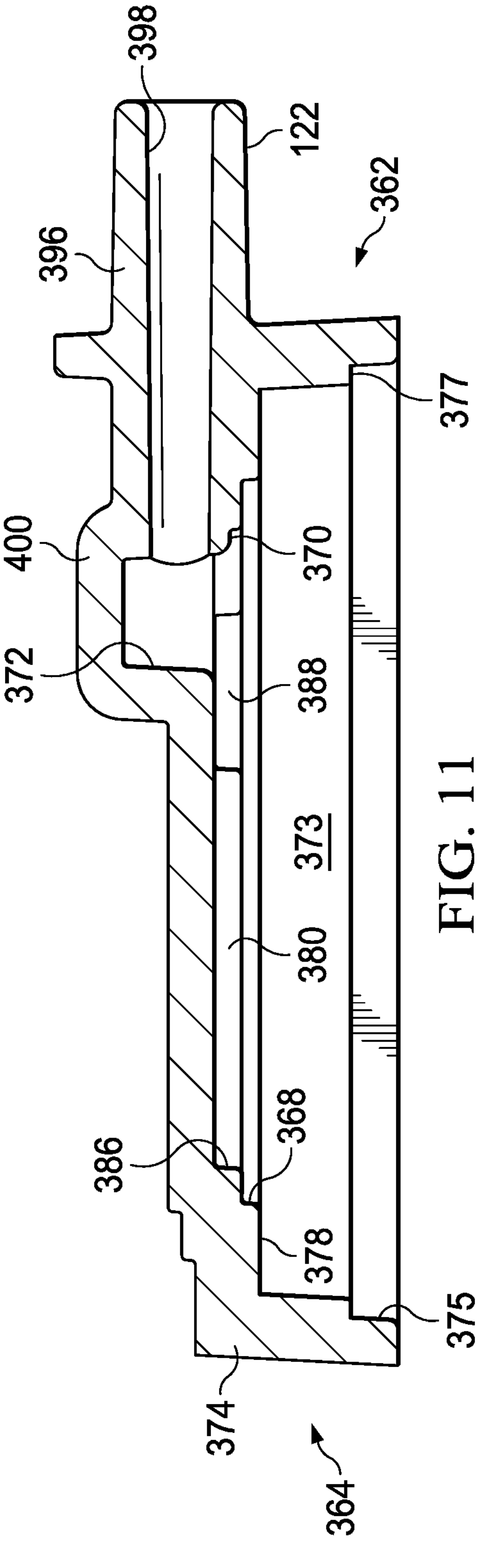
FIG. 11 is a section view taken along line 11-11 of FIG. 10 illustrating additional details that may be associated with some embodiments of the adapter.
Figure 12:
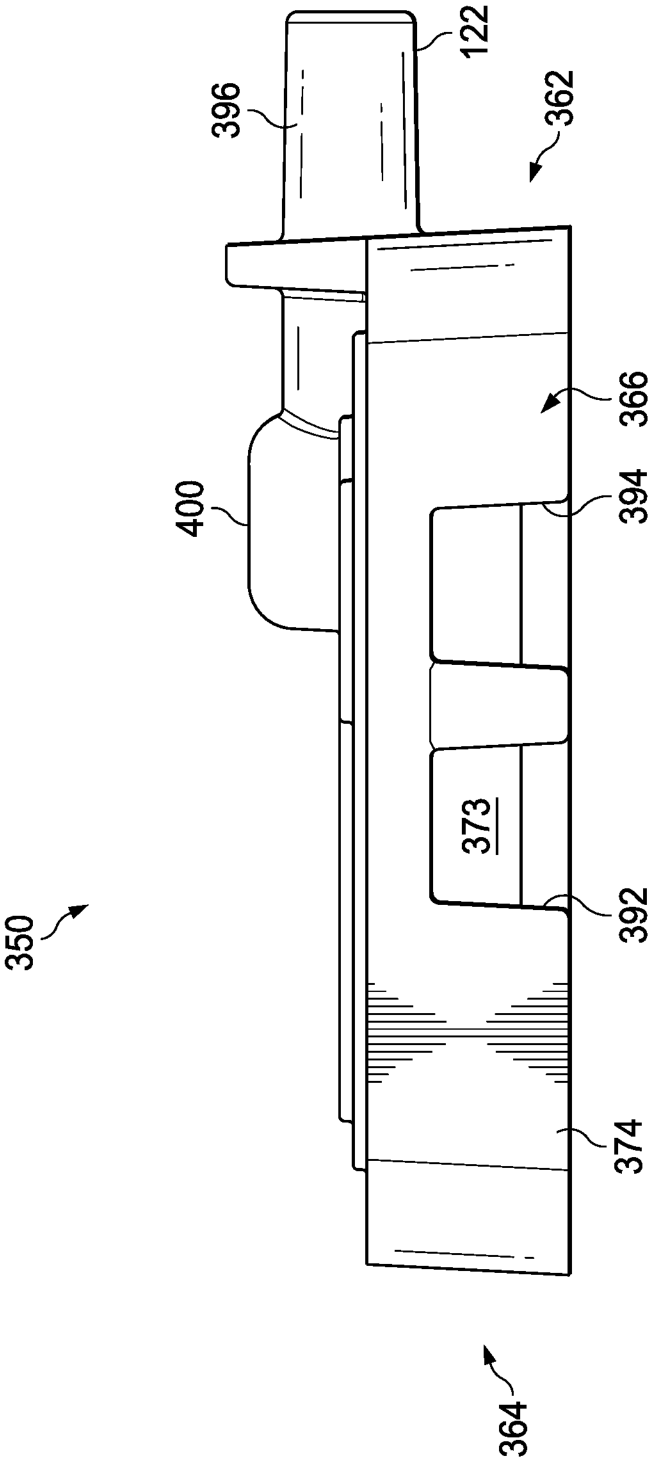
FIG. 12 is a side view illustrating additional details that may be associated with some embodiments of the adapter of FIG. 9.

FIG. 11 is a sectional view illustrating additional details of the adapter 350 taken along line 11-11 of FIG. 10. In some embodiments, the lumen 398 is in fluid communication with the bore 372. Fluid communication from the first side 358 to the second side 360 may occur through the lumen 398, the bore 372, and the third arm 384 of the second recess 370. The second recess 370 can create a channel for the dissipation of heat generated by the pump 148. The bore 372 can be offset from the inlets 202. Preferably, the bore 372 may not be positioned adjacent to an individual inlet 202 of the plurality of inlets 202.

The adapter 350 seals to the inlet plate 201 without contacting the functioning components of the pump 148. For example, the inlet plate 201 can be positioned in the first recess 368 so that the mounting shoulder 204 is adjacent to the shoulder 378. In some embodiments, the first recess 368 may have a depth greater than a distance between the mounting shoulder 204 and a surface of the inlet plate 201. If the mounting shoulder 204 contacts the shoulder 378, a gap may be formed between an interior surface of the first recess 368 and the surface of the inlet plate 201. In other embodiments, no gap may be formed between the interior surface of the first recess 368 and the surface of the inlet plate 201. The mounting shoulder 204 can be coupled to the shoulder 378 of the adapter 350, securing the adapter 350 to the pump 148. In other embodiments, the edge surface 153 can be coupled to the interior surface 373 to secure the adapter 350 to the pump 148.

In operation, the pump 148 can be actuated by applying an electrical current to the electric contacts 352. In response, fluid can be drawn through the lumen 398 into the bore 372, the second recess 370, and the inlets 202. Movement of fluid through the second recess 370 into the inlets 202 moves fluid across the inlet plate 201 of the suction side 154 of the pump 148. The adapter 350 can aggregate fluid flow into the inlets 202 by directing fluid flow from the lumen 398 through the second recess 370 and across the inlet plate 201. Movement of fluid across the inlet plate 201 of the pump 148 through the second recess 370 can dissipate heat generated by the pump 148 using convective cooling. Additional heat dissipation can be achieved through conductive heat transfer between the interior surface 373, the first recess 368, and the shoulder 378 of the adapter 350 and the edge surface 153 and the suction side 154 of the pump 148.

Figure 13:
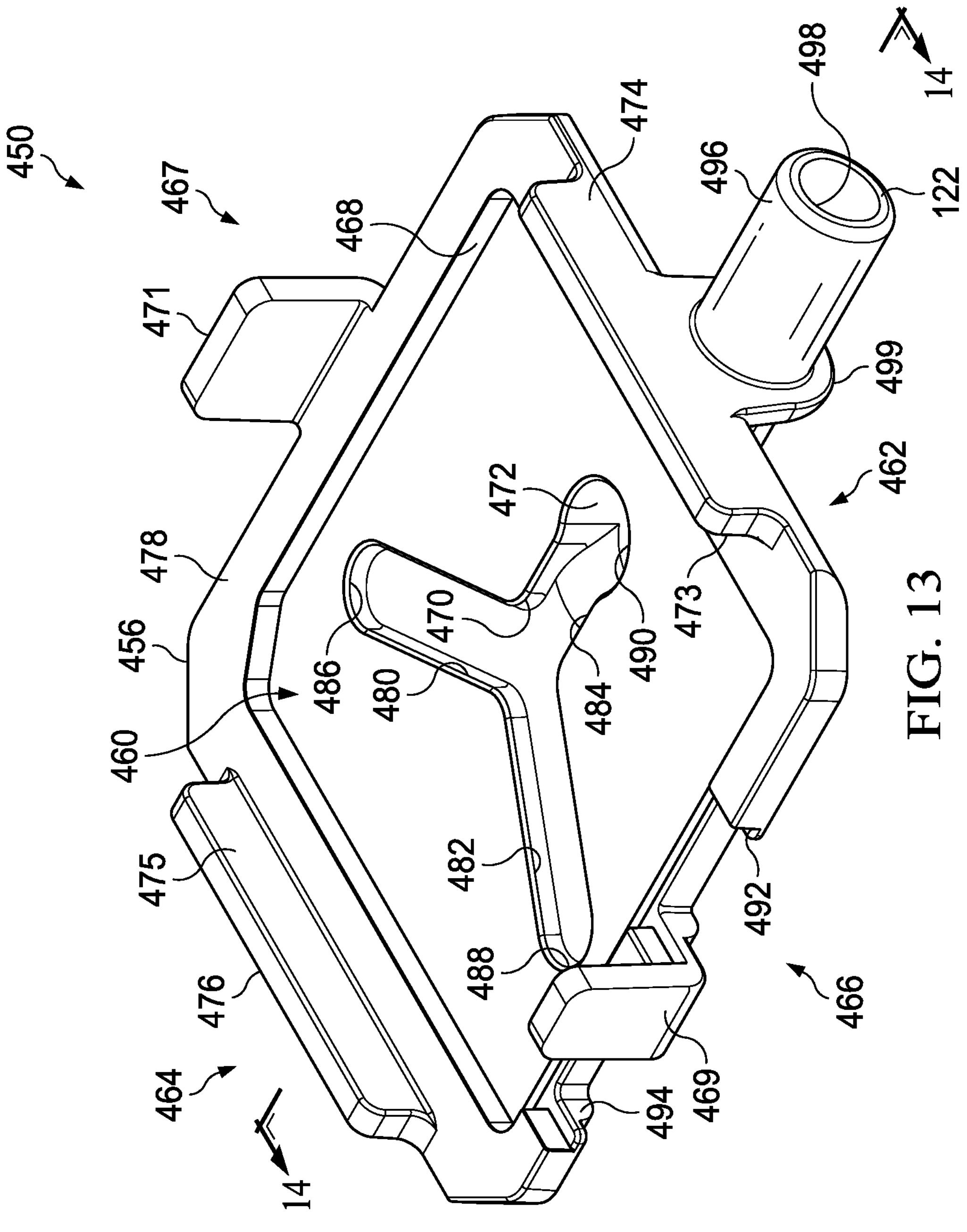
FIG. 13 is a bottom perspective view illustrating additional details that may be associated with another adapter of a therapy device that may be used with the therapy system of FIG. 1.

FIG. 13 is a perspective bottom view illustrating additional details of another fluid aggregator that may be used in some embodiments of the therapy system of FIG. 1. The fluid aggregator may be an adapter 450 and can be coupled to the pump 148. The adapter 450 may have a member, such as a block 456 having a first side 458 and a second side 460. The adapter 450 may have a first end 462 extending between the first side 458 and the second side 460 and a second end 464 opposite the first end 462. The adapter 450 may have a third end 466 perpendicular to and extending from the first end 462 to the second end 464 and a fourth end 467 opposite the third end 466.

In some embodiments, the adapter 450 may have cavity, such as a first recess 468, disposed in the second side 460 and depending into the block 456. The first recess 468 may have an area less than an area of the second side 460. In some embodiments, the first recess 468 may be sized to receive the suction side 154 of the pump 148. For example, the first recess 468 may have an area and a shape such that at least a portion of the suction side 154 of the pump 148 can be received by the first recess 468 without interfering with the operation of the pump 148. In some embodiments, the first recess 468 may be substantially square and form a shoulder 478. The shoulder 478 may substantially surround the first recess 468. The shoulder 478 may extend from an edge of the block 456 to the first recess 468.

The adapter 450 may have a channel, such as a second recess 470, disposed in the first recess 468 and depending into the block 456. The second recess 470 may have an area less than the area of the first recess 468. In some embodiments, the second recess 470 may be disposed near a center of the first recess 468. The second recess 470 may be T-shaped, V-shaped, Y-shaped, circular, square, triangular, or amorphous shaped. In some embodiments, the second recess 470 may have a volume of about 32.75 cubic millimeters. The second recess 470 may have a first arm 480, a second arm 482, and a third arm 484. Each of the first arm 480, the second arm 482, and the third arm 484 may have a first end and a second end 486, 488, 490, respectively. The first end of each of the first arm 480, the second arm 482, and the third arm 484 may be positioned proximate to a center of the block 456. The second end 486, 488, 490 of the first arm 480, the second arm 482, and the third arm 484, respectively, may be spaced from the center of the block 456. For example, the second end 486 of the first arm 480 may be proximate to the intersection of the second end 464 and the fourth end 467. Similarly, the second end 488 of the second arm 482 may be proximate to the intersection of the second end 464 and the third end 466. In some embodiments, the first arm 480, the second arm 482, and the third arm 484 may have a same length between the first end and the second end. In other embodiments, the first arm 480, the second arm 482, and the third arm 484 may have different lengths. In some embodiments, the second end 486, the second end 488, and the second end 490 may be equidistantly spaced from each other. In other embodiments, the second end 486, the second end 488, and the second end 490 may not be equidistantly spaced from each other. The second end 486, the second end 488, and the second end 490 may be rounded. In other embodiments, the second end 486, the second end 488, and the second end 490 may be square, triangular, or amorphous shaped. In some embodiments, the first ends of each of the first arm 480, the second arm 482, and the third arm 484 may be positioned near a center of the block 456.

A fluid lumen such as a bore 472 may depend into and through the block 456. In some embodiments, the bore 472 may be located proximate to the first end 462 of the block 456. For example, the bore 472 may be located at the second end 490 of the third arm 484. The bore 472 may provide fluid communication across the block 456 from the first side 458 to the second side 460. The bore 472 may be positioned in the second recess 470 and have a chamfered transition from the bore 472 to the second recess 470. For example, the bore 472 may intersect a surface of the second recess 470 to form an edge, and the edge can be chamfered.

The adapter 450 may have a first leg or a first projection 474 extending from the second side 460 proximate to the first end 462. The first projection 474 may have a length less than or equal to a length of the first end 462. The first projection 474 may have a height less than or equal to a depth of the pump 148. The first projection 474 may have a first surface 473. The first surface 473 may face the first recess 468 and extend from the shoulder 478 to a height of the first projection 474. The adapter 450 may have a second leg or second projection 476 extending from the second side 460 proximate to the second end 464. The second projection 476 may have a length less than or equal to a length of the second end 464. The second projection may have a height less than or equal to a depth of the pump 148. The second projection 476 may have a second surface 475. The second surface 475 may face the first recess 468 and the first surface 473. The second surface 475 may extend from the shoulder 478 to a height of the second projection 476. The first projection 474 and the second projection 476 may be sized to provide an area for secure attachment of the adapter 450 to the pump 148.

The adapter 450 may have a first notch 492 extending into the third end 466 of the block 456. The first notch 492 may extend into the first recess 468 through the shoulder 478. The first notch 492 may have a depth substantially equal to a depth of the block 456. The adapter 450 may have a second notch 494 extending into the third end 466 of the block 456. The second notch 494 may extend into the first recess 468 through the shoulder 478. The second notch 494 may have a depth substantially equal to a depth of the block 456. The second notch 494 may be proximate to the second projection 476, and the first notch 492 may be proximate to the second notch 494. The first notch 492 and the second notch 494 may be closer to the second projection 476 than to the first projection 474. In some embodiments, the first notch 492 and the second notch 494 can be positioned to receive the electric contacts 152.

The adapter 450 may also include a first guide pin 469 and a second guide pin 471. The first guide pin 469 can be coupled to the third end 466 of the block 456. The first guide pin 469 may be adjacent to the shoulder 478. In some embodiments, the first guide pin 469 may be disposed between the first notch 492 and the second notch 494. The first guide pin 469 may project away from the second side 460 and have a length less than or equal to the depth of the pump 148. In some embodiments, the first guide pin 469 may have a width extending from an edge of the first notch 492 to an adjacent edge of the second notch 494. The second guide pin 471 can be coupled to the fourth end 467 of the block 456. The second guide pin 471 can be adjacent to the shoulder 478. Preferably, the shoulder 478 is unobstructed by the first guide pin 469 and the second guide pin 471. The second guide pin 471 may be disposed proximate to a center of the fourth end 467. The second guide pin 471 may project away from the second side 460 and have a length less than or equal to the depth of the pump 148. The second guide pin 471 may have a width less than or equal to a width of the block 456. The first guide pin 469 and the second guide pin 471 may each have a surface facing the first recess 468. In some embodiments, a distance between the surfaces of the first guide pin 469 and the second guide pin 471 facing the first recess 468 can be substantially equal to a width of the pump 148.

Figure 14:
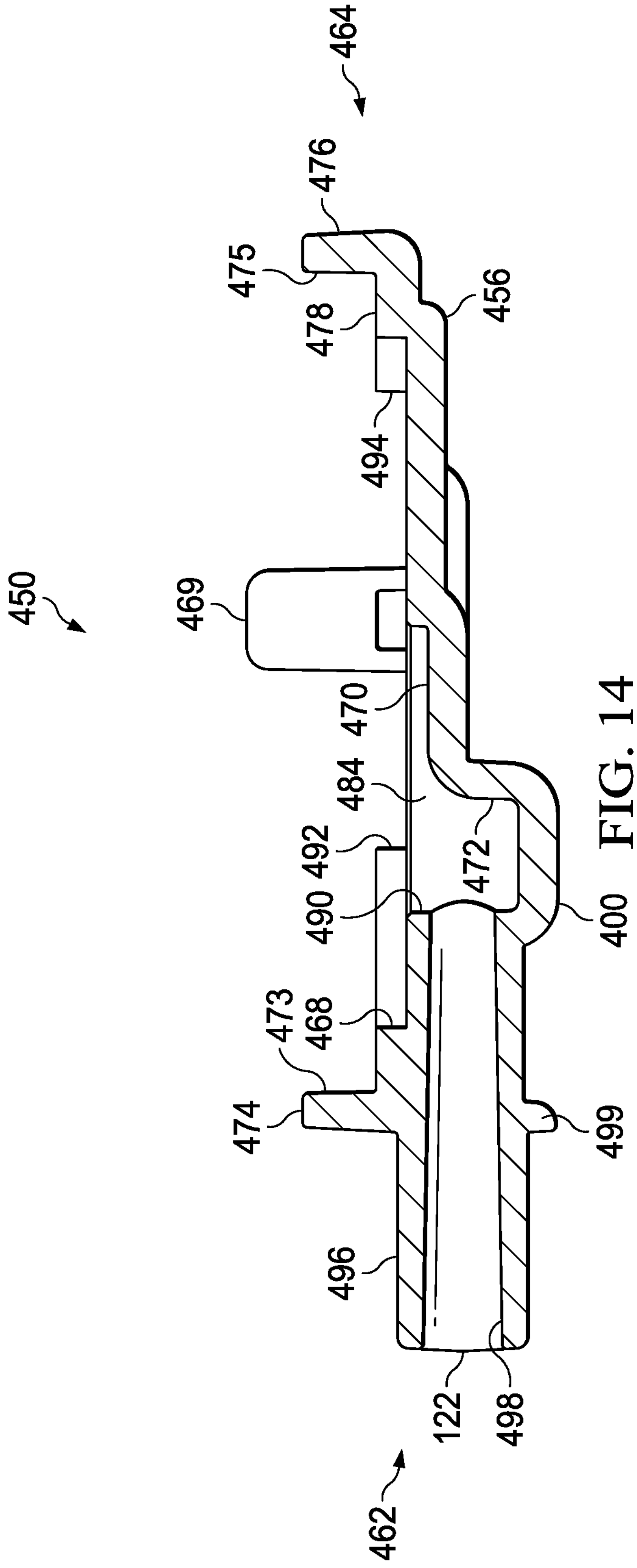
FIG. 14 is a sectional view taken along line 14-14 of FIG. 13 illustrating additional details that may be associated with some embodiments of the adapter of FIG. 13.

FIG. 14 is a sectional view illustrating additional details of the adapter 450 taken along line 13-13 of FIG. 13. In some embodiments, the lumen 498 is in fluid communication with the bore 472. Fluid communication from the first side 458 to the second side 460 may occur through the lumen 498, the bore 472, and the third arm 484 of the second recess 470. The second recess 470 can create a channel for the dissipation of heat generated by the pump 148. The bore 472 can be offset from the inlets 202. Preferably, the bore 472 may not be positioned adjacent to an individual inlet 202 of the plurality of inlets 202.

Figure 15:
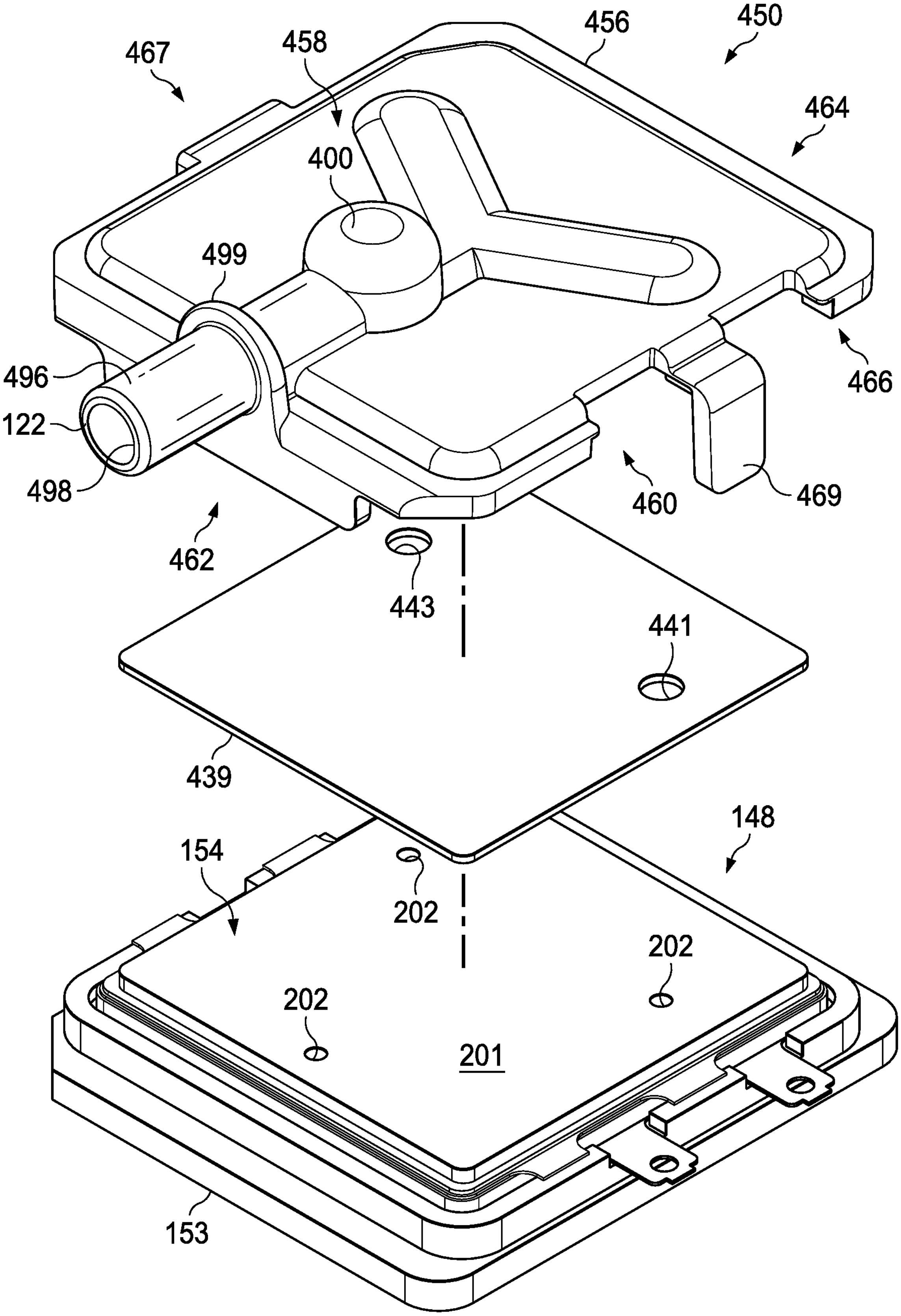
FIG. 15 is a perspective assembly illustrating additional details that may be associated with some embodiments of the adapter of FIG. 13.

FIG. 15 is a perspective assembly view illustrating additional details of the adapter 450. A conduit 496 may be coupled to the first side 458 of the block 456. The conduit 496 may have a lumen 498 extending through the conduit 496. A first end 400 of the conduit 496 may be disposed proximate to the center of the block 456. In some embodiments, the first end 400 of the conduit 496 can be offset toward the first end 462 from the center of the block 456. A second end of the conduit 496 may have the inlet 122. The inlet 122 may project from the block 456. In some embodiments, the inlet 122 may be perpendicular to the first end 462. In some embodiments, the conduit 496 may have a side that tapers from the conduit 496 into the first side 458 of the block 456. In some embodiments, the inlet 122 comprises a horizontal spigot. The inlet 122 may be a tube connector capable of being coupled to a fluid conductor or other device. A vertical support 499 can be coupled to the first side 458 of the adapter 450 proximate to the first end 462. The conduit 496 may pass through the vertical support 499. The vertical support 499 can provide a stop, preventing the conduit 496 from being inserted into another conduit past the position of the vertical support 499.

In some embodiments, the adapter 450 can cover the inlet plate 201 of the pump 148 and translate the suction side 154 of the pump 148 into a vacuum port, such as the inlet 122. The adapter 450 can have a peripheral shape that matches a shape of the edge surface 153. In other embodiments, the peripheral shape of the adapter 450 may not match the edge surface 153. The adapter 450 can be coupled to and seal to the inlet plate 201 of the pump 148 without interfering with the operation of the pump 148. The first guide pin 469 and the second guide pin 471 can align the adapter 450 relative to the pump 148. Preferably, the first guide pin 469 and the second guide pin 471 position the adapter 450 relative to the pump 148 so that an inlet 202 is aligned with the second end 486 of the first arm 480 and another inlet 202 is aligned with the second end 488 of the second arm 482. In some embodiments, the first guide pin 469 may fit between the electrical contacts 152 of the pump 148, and the second guide pin 471 can contact the edge surface 153 of the pump 148 on a side of the pump 148 opposite the electrical contacts 152.

In some embodiments, a coupler, for example, an adhesive 439 can couple the adapter 450 to the pump 148. The adhesive 439 can cover the inlet plate 201 of the pump 148. In some embodiments, a first aperture 441 and a second aperture 443 can be formed through the adhesive 439. Preferably, the first aperture 441 and the second aperture 443 each align with a separate inlet 202. In some embodiments, a third inlet 202 may be covered by the adhesive 439. In some embodiments, covering an inlet 202 with the adhesive 439 that is proximate to the first end 462 of the adapter 450 increases the strength of the seal between the adapter 450 and the inlet plate 201 of the pump 148. As fluid passing through the inlets 202 is aggregated in the pump 148, performance of the pump 148 is not inhibited. The adhesive 439 may be a high temperature adhesive capable of adhering at temperatures of 100° C., for example, a layer of Polar Seal PSTC 5076 DCMA double-sided tape having an area substantially equal to an area of the inlet plate 201 of the pump 148. The adhesive 439 adheres the adapter 450 to the inlet plate 201 of the pump 148. The conduit 496 draws airflow across the copper surface of the inlet plate 201 to reduce overall thermal buildup in the pump 148, maintaining pump output flow efficiency.

The adapter 450 seals to the inlet plate 201 without contacting the functioning components of the pump 148. For example, the inlet plate 201 can be positioned in the first recess 468 so that the mounting shoulder 204 is adjacent to the shoulder 478. In some embodiments, the first recess 468 may have a depth greater than a distance between the mounting shoulder 204 and a surface of the inlet plate 201. In other embodiments, the edge surface 153 can also be coupled to the first surface 473 and the second surface 475 to further secure the adapter 450 to the pump 148.

In operation, the pump 148 can be actuated by applying an electrical current to the electric contacts 152. In response, fluid can be drawn through the lumen 498 into the bore 472, the second recess 470, and the inlets 202. Movement of fluid through the second recess 470 into the inlets 202 moves fluid across the inlet plate 201 of the suction side 154 of the pump 148. The adapter 450 can aggregate fluid flow into the inlets 202 by directing fluid flow from the lumen 498 through the second recess 470 and across the inlet plate 201. Movement of fluid across the inlet plate 201 of the pump 148 through the second recess 470 can dissipate heat generated by the pump 148 using convective cooling. Additional heat dissipation can be achieved through conductive heat transfer between the first surface 473, the first recess 468, and the shoulder 478 of the adapter 450 and the edge surface 153 and the inlet plate 201 of the pump 148. In some embodiments, movement of fluid through the second recess 470 across the inlet plate 201 can maintain the pump 148 at a temperature of approximately 30° C. while providing approximately 125 mmHg of negative pressure and at a temperature of approximately 40° C. while providing approximately 300 mmHg of negative pressure. A thickness of the block 456 can be selected to minimize the total amount of thermal insulation of heat within the pump 148. For example, the block 456 may be injection molded and have an average thickness. In some embodiments, the average thickness from a surface of the first side 458 to a surface of the second side 460 at the first recess 468 can be between about 0.5 mm and about 3 mm. In a preferred embodiment, the average thickness from the surface of the first side 458 to the surface of the second side 460 at the first recess 468 can be about 0.9 mm. Similarly, the average thickness from a surface of the first side 458 to a surface of the second side 460 at the second recess 470 can be between about 0.5 mm and about 3 mm. In a preferred embodiment, the average thickness from the surface of the first side 458 to the surface of the second side 460 at the second recess 470 can be about 0.9 mm.

Each of the fluid aggregators described herein, for example, the adapter 150, the adapter 350, and the adapter 450, can be machined from metal, for example aluminum, stamped from a sheet of metal, can be formed from sintered metal, or 3-D printed from metal. Fluid aggregators formed from metal may have a higher rate of thermal conduction compared to fluid aggregators formed from a polymer material. The fluid aggregators formed from metal can be attached to the pump 148 using a loaded epoxy, for example an Araldite®, Fixmaster®, Masterbond, Devcon®, or other similar adhesive.

Each of the fluid aggregators described herein, for example, the adapter 150, the adapter 350, and the adapter 450, can also be formed from a metal loaded poly carbonate (PC), an acrylonitrile butadiene styrene (ABS) thermoplastic polymer, an ABS polymer blend, or a mixed nylon. For example, the fluid aggregators can be formed from a PC-ABS Makrolon® blend, such as, Makrolon® 2458 Clear. In some embodiments, the fluid aggregators may be transparent, permitting transmission of a visible light. In some embodiments, the ratio of conductive loading of the adapter 150 may be as high as 50%. The ratio of conductive loading can refer to the ability of the material to conduct heat through the material and can also be known as thermal conductivity. The material and the thickness of the block 156, the block 356, and the block 456 can be selected so that the ratio of conductive loading approaches 100%, although inefficiencies can prevent the ratio of conductive loading from being 100%. Preferably, the material and the thickness of the block 156, the block 356, and the block 456 can be selected to prevent heat insulation of the pump 148. In some embodiments, each fluid aggregator can weigh less than about 1 gram. In other embodiments, each fluid aggregator can weigh less than about 0.75 grams, and in still other embodiments, each fluid aggregator can weigh less than about 0.5 grams.

In some embodiments, each of the fluid aggregators, including the adapter 150, the adapter 350, and the adapter 450, can be attached to the pump 148 using a high temperature ultraviolet light curable adhesive, for example, Dymax® Multi-Cure® 9-20801 or Panacol-Elosol GmbH Vitralit® 6137. For example, the adhesive can be applied to first surface 173 of the first projection 174 and the second surface 175 of the second projection 176 that face the first recess 168 of the adapter 150. The pump 148 can be inserted into the adapter 150 between the first projection 174 and the second projection 176. The adhesive can bond the edge surface 153 of the pump 148 to the first surface 173 of the first projection 174 and the second surface 175 of the second projection 176. In another example, the adhesive can be applied to the interior surface 373 of the annular wall 374. The pump 148 can be inserted into the adapter 350. The adhesive can bond the edge surface 153 of the pump 148 to the interior surface 373 of the annular wall 374. In still another example, the adhesive 439 can be applied to the surface of the inlet plate 201. The pump 148 can be inserted between the first projection 474, the second projection 476, the first guide pin 469, and the second guide pin 471 so that the surface of the first recess 368 contacts the adhesive 439, bonding the inlet plate 201 to the first recess 468.

In other embodiments, each of the fluid aggregators, including the adapter 150, the adapter 350, and the adapter 450, can be attached to the pump 148 using a solvent-based curable adhesive, a high temperature pattern-coated adhesive, such as epoxies, acrylates, silicones, a high temperature double-sided adhesive coated polymeric adhesive, such as a polyethylene or polyurethane tape, or a transfer tape, such as Polar Seal PSTC 5076 DCMA tape. A suitable tape may have a polyethylene terephthalate (PET) film backing and a modified acrylic adhesive bonded to the backing. In some embodiments, the adhesive may have a thickness of about 205 micrometers ("μm"). The adhesive can have a peel adhesion between about 5.6 and 14.0 Newtons/centimeter ("N/cm"), a temperature resistance between about 100° C. and 200° C., a tensile strength greater than or equal to 30 N/15 mm, an elongation greater than or equal to 50%, and a static sheer resistance between 125 grams at 70° C. for greater than 10,000 min and 500 grams at 23° C. for greater than 10,000 min based on a bonding area of 20 mm×13 mm to stainless steel with a 10 minute dwell time.

The dimensions of each fluid aggregator, such as the adapter 150, the adapter 350, and the adapter 450, prevents flow bias of the pump 148 and does not restrict the flow of air through the pump 148 or the communication of negative pressure. Each of the adapter 150, the adapter 350, and the adapter 450 can be molded through an injection molding process so that the adapter 150, the adapter 350, and the adapter 450 have the appropriate draft on the bore 172, the bore 372, and the bore 472. For example, if the adapter 150 is injection molded, the diameter of the bore 172 can decrease from the first side 158 to the second side 160, permitting the adapter 150 to be ejected from the mold. The dimensions and tolerances can be reduced if the adapter 150, the adapter 350, and the adapter 450 are machined or sintered. For example, the decreasing diameter of the bore 172 can be eliminated, permitting a generally smaller diameter for an equivalent flow rate. The shape and size of the adapter 150, the adapter 350, and the adapter 450 can be modified as needed to accommodate various pumps provided the second recess 170 and the second recess 370 are aligned with and sealed to the inlets 202 of the pump 148 to ensure that negative pressure is generated and a wall thickness of the adapter 150, the adapter 350, and the adapter 450 are selected to minimize insulation. The seal can be around each discrete inlet 202 or alternatively the seal may be around the perimeter of the pump 148, enclosing a small volume of air between the pump 148 and the adapter 150, the adapter 350, or the adapter 450 to help with convective heat dissipation. In some embodiments, the material of the fluid aggregator can be selected to be more conductive (metallic if necessary) if additional heat reduction is necessary. In some embodiments, the adapter 150, the adapter 350, and the adapter 450 can be integrated into the lid 134 of the container 106.

The systems, apparatuses, and methods described herein may provide significant advantages. For example, the adapter facilitates easy conversion of a positive pressure pump to a negative-pressure generating device while acting as a conduit to transmit and thermally conduct heat away to a heat sink, such as a circuit board or to a thermal scavenging system. The adapter is designed to convert a positive-pressure piezoelectric pump into a negative-pressure source without interfering or modifying the base pump. The adapter may be part of or pre-mounted to a manifold or a printed circuit board. A commercially available pump can then be coupled to the manifold or printed circuit board. Thus, the adapter manages the conversion of a positive-pressure pump to a negative-pressure source and also provides the mechanical location for the negative-pressure source. In some embodiments, a canister may be sealed and contain the pump to create a means to use a positive pressure pump for negative-pressure therapy without the use of an adapter.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 104, the container 106, or both may be eliminated or separated from other components for manufacture or sale. In other example configurations, the controller 112 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A fluid aggregator for aggregating fluid flow into an inlet of a piezoelectric pump, the fluid aggregator comprising:

a member having a first side, a second side opposite the first side, a first end between the first side and the second side, a second end opposite the first end, and a third end perpendicular to and extending from the first end to the second end;

a cavity disposed in the second side and having an area less than an area of the second side;

a channel disposed in the cavity, the channel having an area less than the area of the cavity;

a fluid lumen through the member from the channel to the first side;

the channel comprising a first arm and a second arm, a union of each arm with adjacent arms of the second side being positioned at the fluid lumen;

a conduit coupled to the first side, the conduit having at least one lumen fluidly coupled to the fluid lumen;

a first notch extending into the third end of the member, the first notch having a length extending into the cavity and a depth substantially equal to a depth of the member; and a second notch extending into the third end of the member, the second notch having a length extending into the cavity and a depth substantially equal to a depth of the member.

2. The fluid aggregator of claim 1, the fluid aggregator further comprising:

a first leg extending from the second side and proximate to the first end, the first leg having a length substantially equal to a length of the first end; and a second leg extending from the second side and proximate to the second end, the second leg having a length substantially equal to a length of the second end.

3. The fluid aggregator of claim 2, wherein the first leg has a surface facing the second leg and the second leg has a surface facing the first leg, the surface of the first leg and the surface of the second leg configured to be coupled to the piezoelectric pump.

4. The fluid aggregator of claim 1, wherein the channel further comprises a third arm, a union of each arm with adjacent arms of the channel being positioned at the fluid lumen.

5. The fluid aggregator of claim 4, wherein each arm has a same length.

6. The fluid aggregator of claim 1, wherein the first arm and the second arm comprise a V-shape, an apex of the V being positioned at the fluid lumen.

7. The fluid aggregator of claim 1, wherein the first arm and the second arm comprise a T-shape, the fluid lumen being located at a crossing of the first arm and the second arm.

8. The fluid aggregator of claim 1, wherein the conduit comprises a tube coupled to the first side and having a tube connector projecting from the first end of the member, the tube connector configured to be fluidly coupled to another tube.

9. The fluid aggregator of claim 1, wherein each of the first notch and the second notch is configured to receive an electrical contact of the piezoelectric pump.

10. The fluid aggregator of claim 1, wherein the fluid lumen intersects a surface of the channel to form an edge, the edge being chamfered.

11. The fluid aggregator of claim 1, wherein the fluid aggregator is injection molded.

12. The fluid aggregator of claim 1, wherein the fluid aggregator is thermally conductive and configured to conduct heat away from the piezoelectric pump.

13. The fluid aggregator of claim 12, wherein the fluid aggregator has a 50% conductive loading ratio.

14. The fluid aggregator of claim 1, wherein the fluid aggregator comprises a polymer.

15. The fluid aggregator of claim 1, wherein the fluid aggregator is configured to cover and seal the inlet of the piezoelectric pump without contacting functioning components of the piezoelectric pump.

16. The fluid aggregator of claim 1, wherein:

the piezoelectric pump comprises a heat sink having an outer surface; and the fluid aggregator is configured to cover the outer surface.

17. The fluid aggregator of claim 1, wherein the fluid aggregator weighs less than 1 gram.

18. The fluid aggregator of claim 1, wherein the fluid aggregator is configured to direct fluid flow across a surface of the piezoelectric pump having the inlet, the surface being perpendicular to the inlet.

* * * * *